(12) United States Patent
Steller et al.

(10) Patent No.: US 7,507,788 B2
(45) Date of Patent: Mar. 24, 2009

(54) PEPTIDES AND METHODS FOR CELL DEATH REGULATION

(75) Inventors: Hermann Steller, New York, NY (US); Hyung Don Ryoo, New York, NY (US); Aaron Ciechanover, Haifa (IL); Hedva Gonen, Zichron-Yakov (IL)

(73) Assignees: Rappaport Family Institute for Research in the Medical Sciences, Haifa (IL); Rockefeller Institute, New York, NY (US)

( * ) Notice: Subject to any disclaimer, the term of this patent is extended or adjusted under 35 U.S.C. 154(b) by 0 days.

(21) Appl. No.: 10/431,638

(22) Filed: May 8, 2003

(65) Prior Publication Data

US 2006/0003939 A1 Jan. 5, 2006

Related U.S. Application Data

(60) Provisional application No. 60/378,668, filed on May 9, 2002, provisional application No. 60/448,869, filed on Feb. 24, 2003.

(51) Int. Cl.
*C07K 5/00* (2006.01)
(52) U.S. Cl. .................... 530/300; 424/184.1; 536/23.1
(58) Field of Classification Search ................. 530/300; 424/184.1; 536/23.1
See application file for complete search history.

(56) References Cited

U.S. PATENT DOCUMENTS 5,593,879 A * 1/1997 Steller et al. ................. 435/325
6,469,144 B1 * 10/2002 Ashkenazi ................ 530/387.9

FOREIGN PATENT DOCUMENTS

WO 2001062936 A2 8/2001

OTHER PUBLICATIONS

Bowie (Science, 1990, 257:1306-1310).*
Wing et al, Apr. 2001 (Mechanism Development, 102: 193-203).*
Wing et al, Jan. 2002 (Current Biol, 12: 131-135).*
Goyal et al., "Induction of Apoptosis by Drosophila Reaper, Hid and Grim Through Inhibition of IAP Function," EMBO J. 19:589:597 (2000).
White et al., "Genetic Control of Programmed Cell Death in Drosophila," Science 264:677-683 (1994).
Wu et al., "Structural Analysis of a Functional DIAP1 Fragment Bound to Grim and hid Peptides," Mol. Cell 8:95-104 (2001).
Hedge et al., "Identification of Omi/HtrA2 as a Mitochondrial Apoptotic Serine Protease That Disrupts IAP-Capase Interaction," J. Biol. Chem. 277:432-438 (2002).

Martins et al., "The Serine Protase Omi/Htr/A2 Regulates Apoptosis by Binding XIAP Through a Reaper-Like Motif," J. Biol. Chem. 277:439-444 (2002).
Suzuki et al., "A Serine Protease, HtrA2 is Released From the Mitochrondria and Interacts With the XIAP, Inducing Cell Death," Mol. Cell 8:613-621 (2001).
Verhagen et al., "HtrA2 Promotes Cell Death Through its Serine Protase Activity and its Ability to Antagonize Inhibitor of Apoptosis Proteins," J. Biol. Che,. 277:445-454 (2001).
Yang et al., "Ubiquitin Protein Ligase Activity of IAPs and Their Degradation in Proteasomes in Response to Apoptotic Stimuli," Science 288:874-877 (2000).
Wilson et al., "The DIAP1 Ring Finger Mediates Ubiquitination of Dronc and its Indispensable for Regulating Apoptosis," Nat. Cell. Biol. 4:445-450 (2002).
Christich et al., "The Damage-Responsive Drosophila Gene Sickle Encodes a Novel IAP Binding Protein Similar to But Distinct From Reaper, Grim, and Hid," Curr. Biol. 12:137-140 (2002).
Srinivasula et al., "Sickle, A Novel Drosophila Death Gene in the Reaper/hid/Grim Region, Encodes an IAP Inhibitor Protein," Curr. Biol. 12:125-130 (2000)
Grether et al., "The Head Involution Defective Gene of Drosphila Melanogaster Functions in Progammed Cell Death," Genes Dev. 9:1694-1708 (1995).
White et al., "Cell Killing by the Drosophila Gene Reaper," Science 271:805-807 (1996).
Wing et al., "Distinct Cell Killing Properties of the Drosophila Reaper, Head Incolution Defective, and Grim Genes," Cell Death Differ. 5:930-939 (1998).
Ryoo et al., "Regulation of Drosophila IAP1 Degradation and Apoptosis by Reaper and ubcD1," Nature Cell Biology 4:432-438 (2002).
Goyal, L., "Cell Death Inhibition: Keeping Caspases in Check," Cell 104:805-808 (2001).

* cited by examiner

*Primary Examiner*—Larry R. Helms
*Assistant Examiner*—Minh-Tam Davis
(74) *Attorney, Agent, or Firm*—Nixon Peabody LLP

(57) ABSTRACT

The present invention provides novel peptides, nucleic acids, compounds, compositions and methods for regulating apoptosis, and screening methods for identifying same. Regulation of apoptosis is mediated via IAPi-derived proteins, peptide fragments thereof, and nucleic acids encoding same, stimulating/accelerating or downmodulating/suppressing apoptosis. For stimulation/acceleration of apoptosis, the IAPi-derived proteins or peptide fragments thereof comprise RHG and Trp-box amino acid consensus sequences. Stimulation/acceleration results in self-ubiquitination and auto-degradation of an IAP. For downmodulation/suppression of apoptosis, IAPi-derived proteins or peptide fragments thereof comprising either RHG or Trp-box amino acid consensus sequences, or both, failing to stimulate or suppressing self-ubiquitination and auto-degradation of an IAP, result in suppression of apoptosis.

5 Claims, 14 Drawing Sheets

```
Rpr          1-  M A V A F Y I  -7
Grim         1-  M A I A Y F I  -7
Hid          1-  M A V P F Y L  -7
Skl          1-  M A I P F F I  -7
Smac/Diablo  1-  M A V P I A Q  -7
Omi/HtrA2    1-  M A V P S P P  -7
```

FIG.10

```
Rpr     26- RLRESQWRFLATVVLETLRQYTSCHPKTGR   -55
Grim    80- MSEFGCWDLLAQILCYALRIYSYSSQRQP    -109
Hid-1   95- LYALYEWVRMYQSQQSAPQIFQYPPPSPSC   -124
Hid-2   239- SSAAFGWHGHPHSPFTSTSTPLSAPVAPKM  -268
Hid-3   295- SDHEATWDEFGDRYDNFTAGRERLQEFNGR  -324
Hid-4   385- KPQSFTWPTVVTVFVLAMGCGFFAAR      -410
```

FIG.11

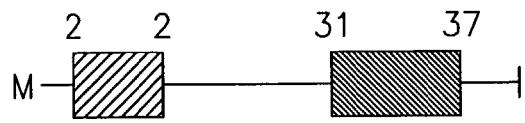

▨ RHG-motif: BIR binding

▨ Trp-box: stimulates IAP auto-ubiquitination(QWRFLAT)

FIG.12

| RPR | − | + | − | − | − | − | − | − |
| --- | --- | --- | --- | --- | --- | --- | --- | --- |
| RPR1−15 (μM) | − | − | 10 | 30 | 100 | − | − | − |
| HID1−15 (μM) | − | − | − | − | − | 10 | 30 | 100 |

DIAP1 →

| GRIM1−15 (μM) | 10 | 30 | 100 | − | − | − |
| --- | --- | --- | --- | --- | --- | --- |
| RPR1−15−TRP (μM) | − | − | − | 10 | 30 | 100 |

DIAP1 →

SEQUENCE LISTING

<160> NUMBER OF SEQ ID NOS: 60

<210> SEQ ID NO 1
<211> LENGTH: 14
<212> TYPE: PRT
<213> ORGANISM: Drosophila melanogaster

<400> SEQUENCE: 1

Ala Val Ala Phe Tyr Ile Pro Asp Gln Ala Thr Leu Leu Arg
1               5                   10

<210> SEQ ID NO 2
<211> LENGTH: 14
<212> TYPE: PRT
<213> ORGANISM: Drosophila melanogaster

<400> SEQUENCE: 2

Ala Val Pro Phe Tyr Leu Pro Glu Gly Gly Ala Asp Asp Val
1               5                   10

<210> SEQ ID NO 3
<211> LENGTH: 14
<212> TYPE: PRT
<213> ORGANISM: Drosophila melanogaster

<400> SEQUENCE: 3

Ala Ile Ala Tyr Phe Ile Pro Asp Gln Ala Gln Leu Leu Ala
1               5                   10

<210> SEQ ID NO 4
<211> LENGTH: 15
<212> TYPE: PRT
<213> ORGANISM: Homo sapiens

<400> SEQUENCE: 4

Ala Val Pro Ile Ala Asn Lys Ser Glu Pro His Ser Leu Ser Ser
1               5                   10                  15

<210> SEQ ID NO 5
<211> LENGTH: 15
<212> TYPE: PRT
<213> ORGANISM: Homo sapiens

<400> SEQUENCE: 5

Ala Val Pro Ile Ala Gln Lys Ser Glu Pro His Ser Leu Ser Asn
1               5                   10                  15

<210> SEQ ID NO 6
<211> LENGTH: 15
<212> TYPE: PRT
<213> ORGANISM: Drosophila melanogaster

<400> SEQUENCE: 6

Ala Val Pro Ser Pro Pro Pro Ala Ser Pro Arg Ser Asn Tyr Asn
1               5                   10                  15

<210> SEQ ID NO 7
<211> LENGTH: 15
<212> TYPE: PRT
<213> ORGANISM: Homo sapiens

<400> SEQUENCE: 7

Ala Val Pro Ala Pro Pro Pro Thr Ser Pro Arg Ser Gln Tyr Asn

```
1               5              10             15

<210> SEQ ID NO 8
<211> LENGTH: 4
<212> TYPE: PRT
<213> ORGANISM: Drosophila melanogaster

<400> SEQUENCE: 8

Ala Val Pro Phe
1

<210> SEQ ID NO 9
<211> LENGTH: 7
<212> TYPE: PRT
<213> ORGANISM: Drosophila melanogaster

<400> SEQUENCE: 9

Ala Val Pro Phe Tyr Leu Pro
1               5

<210> SEQ ID NO 10
<211> LENGTH: 8
<212> TYPE: PRT
<213> ORGANISM: Drosophila melanogaster

<400> SEQUENCE: 10

Ala Val Pro Phe Tyr Leu Pro Glu
1               5

<210> SEQ ID NO 11
<211> LENGTH: 3
<212> TYPE: PRT
<213> ORGANISM: Drosophila melanogaster

<400> SEQUENCE: 11

Phe Tyr Leu
1

<210> SEQ ID NO 12
<211> LENGTH: 8
<212> TYPE: PRT
<213> ORGANISM: Drosophila melanogaster

<400> SEQUENCE: 12

Ala Val Ala Phe Tyr Ile Pro Asp
1               5

<210> SEQ ID NO 13
<211> LENGTH: 45
<212> TYPE: DNA
<213> ORGANISM: Drosophila melanogaster

<400> SEQUENCE: 13
atggcagtgg cattctacat acccgatcag gcgactctgt tgcgg              45

<210> SEQ ID NO 14
<211> LENGTH: 45
<212> TYPE: DNA
<213> ORGANISM: Drosophila melanogaster

<400> SEQUENCE: 14
atggccgtgc cctttattt gcccgagggc ggcgccgatg acgta               45

<210> SEQ ID NO 15
```

-continued

```
<211> LENGTH: 45
<212> TYPE: DNA
<213> ORGANISM: Drosophila melanogaster

<400> SEQUENCE: 15
atggccatcg cctatttcat acccgaccag gcccaattgt tggcc          45

<210> SEQ ID NO 16
<211> LENGTH: 45
<212> TYPE: DNA
<213> ORGANISM: Homo sapiens

<400> SEQUENCE: 16
gcggttccta ttgcacagaa atcagagcct cattcccttca gtagt          45

<210> SEQ ID NO 17
<211> LENGTH: 45
<212> TYPE: DNA
<213> ORGANISM: Homo sapiens

<400> SEQUENCE: 17
gcggttccta ttgctcagaa atcggagcct cattctctca gtaac          45

<210> SEQ ID NO 18
<211> LENGTH: 45
<212> TYPE: DNA
<213> ORGANISM: Drosophila melanogaster

<400> SEQUENCE: 18
gccgtcccta gcccgccgcc cgcttctccc cggagtcagt acaac          45

<210> SEQ ID NO 19
<211> LENGTH: 45
<212> TYPE: DNA
<213> ORGANISM: Homo sapiens

<400> SEQUENCE: 19
gctgttcctg ctccgccacc cacttctccc cggagccagt acaat          45

<210> SEQ ID NO 20
<211> LENGTH: 12
<212> TYPE: DNA
<213> ORGANISM: Drosophila melanogaster

<400> SEQUENCE: 20
gccgtgccct tt                                              12

<210> SEQ ID NO 21
<211> LENGTH: 18
<212> TYPE: DNA
<213> ORGANISM: Drosophila melanogaster

<400> SEQUENCE: 21
gccgtgccct tttatttg                                        18

<210> SEQ ID NO 22
<211> LENGTH: 24
<212> TYPE: DNA
<213> ORGANISM: Drosophila melanogaster

<400> SEQUENCE: 22
gccgtgccct tttatttgcc cgag                                 24
```

```
<210> SEQ ID NO 23
<211> LENGTH: 9
<212> TYPE: DNA
<213> ORGANISM: Drosophila melanogaster

<400> SEQUENCE: 23 ttttatttg                                                                9

<210> SEQ ID NO 24
<211> LENGTH: 21
<212> TYPE: DNA
<213> ORGANISM: Drosophila melanogaster

<400> SEQUENCE: 24
gcagtggcat tctacatacc c                                                 21

<210> SEQ ID NO 25
<211> LENGTH: 35
<212> TYPE: PRT
<213> ORGANISM: Drosophila melanogaster

<400> SEQUENCE: 25

Arg Leu Arg Glu Ser Gln Trp Arg Phe Leu Ala Thr Val Val Leu Glu
1               5                   10                  15

Thr Leu Arg Gln Tyr Thr Ser Cys His Pro Lys Thr Gly Arg Lys Ser
            20                  25                  30

Gly Lys Tyr
        35

<210> SEQ ID NO 26
<211> LENGTH: 39
<212> TYPE: PRT
<213> ORGANISM: Drosophila melanogaster

<400> SEQUENCE: 26

Ser Glu Phe Gly Cys Trp Asp Leu Leu Ala Gln Ile Phe Cys Tyr Ala
1               5                   10                  15

Leu Arg Ile Tyr Ser Tyr Ser Ser Ser Gln Arg Gln Pro Thr Val Ile
            20                  25                  30

Gly Ile Ser Phe Glu Ile Ser
        35

<210> SEQ ID NO 27
<211> LENGTH: 7
<212> TYPE: PRT
<213> ORGANISM: Drosophila melanogaster

<400> SEQUENCE: 27

Gln Trp Arg Phe Leu Ala Thr
1               5

<210> SEQ ID NO 28
<211> LENGTH: 10
<212> TYPE: PRT
<213> ORGANISM: Drosophila melanogaster

<400> SEQUENCE: 28

Gln Trp Arg Phe Leu Ala Thr Val Val Leu
1               5                   10

<210> SEQ ID NO 29
<211> LENGTH: 10
<212> TYPE: PRT
```

<213> ORGANISM: Drosophila melanogaster

<400> SEQUENCE: 29

Gln Leu Arg Ser Ser Thr Val Val Leu
1               5                   10

<210> SEQ ID NO 30
<211> LENGTH: 30
<212> TYPE: DNA
<213> ORGANISM: Drosophila melanogaster

<400> SEQUENCE: 30
cagtggagat tcctggccac cgtcgtcctg                                    30

<210> SEQ ID NO 31
<211> LENGTH: 30
<212> TYPE: DNA
<213> ORGANISM: Drosophila melanogaster

<400> SEQUENCE: 31
tgctgggatc ttttggccca gatcttgtgc                                    30

<210> SEQ ID NO 32
<211> LENGTH: 21
<212> TYPE: DNA
<213> ORGANISM: Drosophila melanogaster

<400> SEQUENCE: 32
cagtggagat tcctggccac c                                             21

<210> SEQ ID NO 33
<211> LENGTH: 30
<212> TYPE: DNA
<213> ORGANISM: Drosophila melanogaster

<400> SEQUENCE: 33
cagtggagat tcctggccac cgtcgtcctg                                    30

<210> SEQ ID NO 34
<211> LENGTH: 30
<212> TYPE: DNA
<213> ORGANISM: Drosophila melanogaster

<400> SEQUENCE: 34
cagttgagat cttcgtccac cgtcgtcctg                                    30

<210> SEQ ID NO 35
<211> LENGTH: 49
<212> TYPE: PRT
<213> ORGANISM: Drosophila melanogaster

<400> SEQUENCE: 35

Met Ala Val Ala Phe Tyr Ile Pro Asp Gln Ala Thr Leu Leu Arg Leu
1               5                   10                  15

Arg Glu Ser Gln Trp Arg Phe Leu Ala Thr Val Val Leu Glu Thr Leu
            20                  25                  30

Arg Gln Tyr Thr Ser Cys His Pro Lys Thr Gly Arg Lys Ser Gly Lys
        35                  40                  45

Tyr

<210> SEQ ID NO 36
<211> LENGTH: 45

```
<212> TYPE: PRT
<213> ORGANISM: Drosophila melanogaster

<400> SEQUENCE: 36

Met Ala Val Pro Phe Tyr Leu Pro Glu Gly Gly Ala Asp Asp Val Leu
1               5                   10                  15

Tyr Ala Leu Tyr Glu Trp Val Arg Met Tyr Gln Ser Gln Gln Ser Ala
            20                  25                  30

Pro Gln Ile Phe Gln Tyr Pro Pro Ser Pro Ser Cys
        35                  40                  45

<210> SEQ ID NO 37
<211> LENGTH: 54
<212> TYPE: PRT
<213> ORGANISM: Drosophila melanogaster

<400> SEQUENCE: 37

Met Ala Ile Ala Tyr Phe Ile Pro Asp Gln Ala Gln Leu Leu Ala Ser
1               5                   10                  15

Glu Phe Gly Cys Trp Asp Leu Leu Ala Gln Ile Phe Cys Tyr Ala Leu
            20                  25                  30

Arg Ile Tyr Ser Tyr Ser Ser Ser Gln Arg Gln Pro Thr Val Ile Gly
        35                  40                  45

Ile Ser Phe Glu Ile Ser
    50

<210> SEQ ID NO 38
<211> LENGTH: 14
<212> TYPE: PRT
<213> ORGANISM: Drosophila melanogaster

<400> SEQUENCE: 38

Ala Val Pro Phe Tyr Leu Pro Gln Trp Arg Phe Leu Ala Thr
1               5                   10

<210> SEQ ID NO 39
<211> LENGTH: 18
<212> TYPE: PRT
<213> ORGANISM: Drosophila melanogaster

<400> SEQUENCE: 39

Ala Val Pro Phe Tyr Leu Pro Glu Ala Ala Ala Gln Trp Arg Phe Leu
1               5                   10                  15

Ala Thr

<210> SEQ ID NO 40
<211> LENGTH: 24
<212> TYPE: PRT
<213> ORGANISM: Drosophila melanogaster

<400> SEQUENCE: 40

Ala Val Ala Phe Tyr Ile Pro Asp Gln Ala Thr Leu Leu Arg Gln Trp
1               5                   10                  15

Arg Phe Leu Ala Thr Val Val Leu
            20

<210> SEQ ID NO 41
<211> LENGTH: 18
<212> TYPE: PRT
<213> ORGANISM: Drosophila melanogaster

<400> SEQUENCE: 41
```

```
Ala Val Ala Phe Tyr Ile Pro Asp Gln Leu Arg Ser Ser Ser Thr Val
1               5                   10                  15

Val Leu

<210> SEQ ID NO 42
<211> LENGTH: 18
<212> TYPE: PRT
<213> ORGANISM: Drosophila melanogaster

<400> SEQUENCE: 42

Ala Val Pro Phe Tyr Leu Pro Glu Gln Trp Arg Phe Leu Ala Thr Val
1               5                   10                  15

Val Leu

<210> SEQ ID NO 43
<211> LENGTH: 18
<212> TYPE: PRT
<213> ORGANISM: Drosophila melanogaster

<400> SEQUENCE: 43

Ala Val Pro Phe Tyr Leu Pro Glu Gln Leu Arg Ser Ser Ser Thr Val
1               5                   10                  15

Val Leu

<210> SEQ ID NO 44
<211> LENGTH: 22
<212> TYPE: PRT
<213> ORGANISM: Drosophila melanogaster

<400> SEQUENCE: 44

Ala Val Pro Phe Tyr Leu Pro Glu Gln Ala Thr Leu Gln Trp Arg Phe
1               5                   10                  15

Leu Ala Thr Val Val Leu
            20

<210> SEQ ID NO 45
<211> LENGTH: 14
<212> TYPE: PRT
<213> ORGANISM: Drosophila melanogaster

<400> SEQUENCE: 45

Ala Val Pro Phe Gln Trp Arg Phe Leu Ala Thr Val Val Leu
1               5                   10

<210> SEQ ID NO 46
<211> LENGTH: 14
<212> TYPE: PRT
<213> ORGANISM: Drosophila melanogaster

<400> SEQUENCE: 46

Ala Val Pro Phe Tyr Leu Pro Gln Trp Arg Phe Leu Ala Thr
1               5                   10

<210> SEQ ID NO 47
<211> LENGTH: 10
<212> TYPE: PRT
<213> ORGANISM: Drosophila melanogaster

<400> SEQUENCE: 47

Phe Tyr Leu Gln Trp Arg Phe Leu Ala Thr
1               5                   10
```

```
<210> SEQ ID NO 48
<211> LENGTH: 147
<212> TYPE: DNA
<213> ORGANISM: Drosophila melanogaster

<400> SEQUENCE: 48
atggcagtgg cattctacat acccgatcag gcgactctgt tgcggttgcg ggagtcacag      60
tggagattcc tggccaccgt cgtcctggaa accctgcgcc agtacacttc atgtcatccg     120
aagaccggaa gaaagtccgg caaatat                                         147

<210> SEQ ID NO 49
<211> LENGTH: 135
<212> TYPE: DNA
<213> ORGANISM: Drosophila melanogaster

<400> SEQUENCE: 49
atggccgtgc cctttatttt gcccgagggc ggcgccgatg acgtactata cgccctctac      60
gagtgggtca ggatgtacca gagccagcag agtgccccgc aaatcttcca gtatccgccg     120
ccaagcccct cttgc                                                      135

<210> SEQ ID NO 50
<211> LENGTH: 162
<212> TYPE: DNA
<213> ORGANISM: Drosophila melanogaster

<400> SEQUENCE: 50
atggccatcg cctatttcat acccgaccag gcccaattgt tggcctcgga gtttggatgc      60
tgggatcttt tggcccagat cttgtgctac gctctgcgaa tctacagcta cagttcgagc     120
cagcgtcaac cgacggtcat tcagatatcc ttcgagatca gc                        162

<210> SEQ ID NO 51
<211> LENGTH: 48
<212> TYPE: DNA
<213> ORGANISM: Drosophila melanogaster

<400> SEQUENCE: 51
gccgtgccct tttatttgcc cgagggccag tggagattcc tggccacc                   48

<210> SEQ ID NO 52
<211> LENGTH: 54
<212> TYPE: DNA
<213> ORGANISM: Drosophila melanogaster
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: y is t or c
<220> FEATURE:
<221> NAME/KEY: misc_feature
<222> LOCATION: (15)..(15)
<223> OTHER INFORMATION: y is t or c
<220> FEATURE:
<221> NAME/KEY: misc_feature
```

```
<222> LOCATION: (16)..(16)
<223> OTHER INFORMATION: y is t or c
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: r is a or g
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: r is a or g
<220> FEATURE:
<221> NAME/KEY: misc_feature
<222> LOCATION: (40)..(40)
<223> OTHER INFORMATION: m is a or c
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: y is t or c
<220> FEATURE:
<221> NAME/KEY: misc_feature
<222> LOCATION: (46)..(46)
<223> OTHER INFORMATION: y is t or c
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t

<400> SEQUENCE: 52
gcngtnccnt tytayytncc ngargcngcn gcncartggm gnttyytngc nacn            54

<210> SEQ ID NO 53
<211> LENGTH: 75
<212> TYPE: DNA
<213> ORGANISM: Drosophila melanogaster

<400> SEQUENCE: 53
gcagtggcat tctacatacc cgatcaggcg actctgttgc ggttgcagtg gagattcctg      60
gccaccgtcg tcctg                                                      75

<210> SEQ ID NO 54
<211> LENGTH: 54
<212> TYPE: DNA
```

```
-continued

<213> ORGANISM: Drosophila melanogaster

<400> SEQUENCE: 54
gcagtggcat tctacatacc cgatcagttg agatcttcgt ccaccgtcgt cctg       54

<210> SEQ ID NO 55
<211> LENGTH: 54
<212> TYPE: DNA
<213> ORGANISM: Drosophila melanogaster

<400> SEQUENCE: 55
gccgtgccct tttatttgcc cgagcagtgg agattcctgg ccaccgtcgt cctg       54

<210> SEQ ID NO 56
<211> LENGTH: 54
<212> TYPE: DNA
<213> ORGANISM: Drosophila melanogaster

<400> SEQUENCE: 56
gccgtgccct tttatttgcc cgagcagttg agatcttcgt ccaccgtcgt cctg       54

<210> SEQ ID NO 57
<211> LENGTH: 63
<212> TYPE: DNA
<213> ORGANISM: Drosophila melanogaster

<400> SEQUENCE: 57
gccgtgccct tttatttgcc cgagcaggcg actcagtgga gattcctggc caccgtcgtc  60
ctg                                                                63

<210> SEQ ID NO 58
<211> LENGTH: 42
<212> TYPE: DNA
<213> ORGANISM: Drosophila melanogaster

<400> SEQUENCE: 58
gccgtgccct ttcagtggag attcctggcc accgtcgtcc tg                    42

<210> SEQ ID NO 59
<211> LENGTH: 39
<212> TYPE: DNA
<213> ORGANISM: Drosophila melanogaster

<400> SEQUENCE: 59
gccgtgccct tttatttgca gtggagattc ctggccacc                        39

<210> SEQ ID NO 60
<211> LENGTH: 27
<212> TYPE: DNA
<213> ORGANISM: Drosophila melanogaster

<400> SEQUENCE: 60
tatttgcagt ggagattcct ggccacc                                     27
```

US 7,507,788 B2

PEPTIDES AND METHODS FOR CELL DEATH REGULATION

CROSS-REFERENCE TO RELATED APPLICATIONS

This application claims the priority of Provisional Application No. 60/378,668, filed May 9, 2002, and Provisional Application No. 60/448,869, filed Feb. 24, 2003, the contents of which are incorporated herein by reference.

FIELD OF THE INVENTION

This invention provides compounds and methods for modulating cellular apoptosis, and methods of screening for such compounds. The present invention provides IAPi-derived molecules that stimulate, accelerate, inhibit or abrogate cellular apoptosis. The present invention also provides molecules comprising a peptide comprising an N-terminal RHG and/or a Trp-box amino acid consensus sequence of an IAPi protein, or a fragment thereof, functioning in modulating cellular apoptosis and genetic screening methods which identify agents that modulate apoptotic cell death.

BACKGROUND OF THE INVENTION

In all metazoans programmed cell death or apoptosis, is essential for proper development and maintenance of body homeostasis[1]. Apoptosis is triggered by caspases, members of a cysteine protease family that, when activated, lead to the distinct cellular changes observed in many, if not all, dying cells[2]. The decision to trigger apoptosis depends on the balance between factors that activate caspases and those that inhibit them. Inhibitor of Apoptosis Proteins (IAPs) are negative regulators of apoptosis, which bind to caspases and inhibit their activity[3]. Consistent with this role, inhibition of IAPs has been found to be an important step leading to caspase activation in mammals and *Drosophila*[3].

Various disease states occur due to aberrant regulation of programmed cell death in an organism. For example, defects that result in a decreased level of apoptosis in a tissue as compared to the normal level required to maintain the steady-state of the tissue can result in an increased number of cells in the tissue. Such a mechanism of increasing cell numbers has been identified in various cancers, where the formation of a tumor occurs not because the cancer cells necessarily are dividing more rapidly than their normal counterparts, but because the cells are not dying at their normal rate. The first gene identified as being involved in a cell death pathway, the bcl-2 gene, was identified in cancer cells and was shown to function by decreasing the likelihood that cells expressing the gene would undergo apoptosis.

In comparison to cancer, where the likelihood of a cell undergoing apoptosis is decreased, various pathologies are associated with tissues containing cells undergoing a higher than normal amount of apoptosis. For example, increased levels of apoptosis are observed in various neuropathologies, including Parkinson's disease, Multiple Sclerosis, Alzheimer's disease, Huntington's disease and the encephalopathy associated with acquired immunodeficiency disease (AIDS). Since nerve cells generally do not divide in adults and, therefore, new cells are not available to replace the dying cells, the nerve cell death occurring in such diseases results in the progressively deteriorating condition of patients suffering from the disease.

The important role of IAPs in the regulation of apoptosis is evident from genetic studies in *Drosophila*. The *Drosophila* IAP1 (diap1) is encoded by the thread (th) locus. In loss of function diap1 mutants, apoptosis occurs in virtually all cells during early stages of embryogenesis[4]. The anti-apoptotic function of diap1 is blocked by IAP inhibitor (IAPi) proteins such as REAPER (RPR), HEAD INVOLUTION DEFECTIVE (HID) and GRIM[5-7], forming an RHG family of proteins. IAP inhibition by RHG proteins is similarly crucial during apoptosis in mammals; the mitochondrially localized mammalian RHG proteins Smac/DIABLO and HtrA2 are released into the cytoplasm following apoptotic stimuli and relieve caspase inhibition by IAPs[10-15].

SUMMARY OF THE INVENTION

This invention provides, in one embodiment, peptides, compounds and compositions comprising an RHG and Trp-box amino acid consensus sequence, or a fragment thereof, and methods for IAPi-mediated regulation of cellular apoptosis.

In another embodiment, the invention provides a polynucleotide, which encodes an N-terminal RHG amino acid consensus sequence and a Trp-box amino acid consensus sequence of an IAPi protein, or a fragment thereof. The invention also provides for a polynucleotide encoding for a Trp-box amino acid consensus sequence of an IAPi protein, or a fragment thereof, or a polynucleotide encoding for an RHG amino acid consensus sequence of an IAPi protein, or a fragment thereof, in additional embodiments.

The invention provides, in additional embodiments, vectors comprising polynucleotides encoding for an N-terminal RHG amino acid consensus sequence and a Trp-box amino acid consensus sequence of an IAPi protein, or a fragment thereof, polynucleotides encoding for an N-terminal RHG amino acid consensus sequence of an IAPi protein, or a fragment thereof, or polynucleotides encoding for a Trp-box amino acid consensus sequence of an IAPi protein, or a fragment thereof.

In another embodiment, the invention provides a peptide comprising an N-terminal RHG amino acid consensus sequence and a Trp-box amino acid consensus sequence of an IAPi protein, or a fragment thereof.

In other embodiments, the invention provides for a peptide comprising a Trp-box amino acid consensus sequence of an IAPi protein, or a peptide comprising an N-terminal RHG amino acid consensus sequence of an IAPi protein, or fragments thereof.

In another embodiment, there is provided a composition comprising a polynucleotide or peptide of the invention.

The present invention provides, in another embodiment, a method of stimulating or accelerating apoptosis. The method comprises the step of contacting a cell with an IAPi-derived molecule. In one embodiment, the IAPi-derived molecule is a polynucleotide encoding for an RHG amino acid consensus sequence, or a fragment thereof, and a Trp-box amino acid consensus sequence, or a fragment thereof, of an IAPi protein. In another embodiment, the IAPi-derived molecule is a peptide comprising an RHG amino acid consensus sequence, or a fragment thereof, and a Trp-box amino acid consensus sequence, or a fragment thereof, of an IAPi protein. In another embodiment, the method is effected by compositions comprising the above polynucleotide or peptide.

The present invention provides, in another embodiment, a method of stimulating IAP self-ubiquitination within a cell, comprising the step of contacting a cell with an IAPi-derived molecule. The IAPi-derived molecule comprises polynucleotides encoding and peptides comprising an RHG amino acid consensus sequence, or a fragment thereof, and a Trp-box amino acid consensus sequence, or a fragment thereof, of an IAPi protein, in other embodiments of the invention. According to this aspect of the invention, the method may be effected by compositions comprising the above polynucleotide or peptide.

The invention also provides, in another embodiment, a method of inhibiting apoptosis. The method comprises contacting a cell with an IAPi-derived molecule, which, according to this aspect of the invention comprises either the Trp-box amino acid consensus sequence, or a fragment thereof, or the N-terminal RHG amino acid consensus sequence, or a fragment thereof, of the IAPi protein.

The invention also provides, in another embodiment, a method of inhibiting ubiquitination and/or degradation of an IAP. The method comprises contacting a cell with an IAPi-derived molecule, which, according to this aspect of the invention comprises either the Trp-box amino acid consensus sequence, or a fragment thereof, or the N-terminal RHG amino acid consensus sequence, or a fragment thereof, of the IAPi protein.

The present invention provides, in another embodiment, a screening method for identifying agents that modulate IAP protein levels. The method comprises co-expressing in an expression system a candidate agent and an IAP, and evaluating IAP protein levels, wherein modulation of IAP protein levels thereby identifies a modulating agent.

The present invention provides a screening method for identifying agents that diminish or abrogate IAP protein levels, the method comprising contacting the candidate agent with an IAP in a system allowing for IAP expression, under conditions which allow for IAP ubiquitination, and evaluating IAP ubiquitination, wherein ubiquitination of IAP protein thereby identifies an agent that diminishes or abrogates IAP protein levels.

The invention also provides, in another embodiment, a screening method for identifying agents that stimulate or accelerate apoptosis. The method comprises co-expressing in an expression system a candidate agent and an IAP, and evaluating IAP protein level or activity, wherein diminished IAP levels or activity identifies the agent as stimulating or accelerating apoptosis.

The invention also provides in another embodiment, a screening method for identifying agents that stimulate or accelerate apoptosis. The method comprises contacting the candidate agent with an IAP in a system allowing for IAP expression, under conditions which allow for IAP ubiquitination and/or degradation, and evaluating IAP ubiquitination and/or degradation, wherein increased ubiquitination and/or degradation of the IAP protein thereby identifies the agent as stimulating or accelerating apoptosis.

The invention also provides in another embodiment, a screening method for identifying agents that inhibit or abrogate apoptosis. The method comprises co-expressing in an expression system a candidate agent and an IAP, and evaluating IAP protein level or activity, wherein increased IAP levels or activity identifies the agent as inhibiting or abrogating apoptosis.

The invention also provides in another embodiment, a screening method for identifying agents that inhibit or abrogate apoptosis. The method comprises contacting the candidate agent with an IAP in a system allowing for IAP expression, under conditions which allow for IAP ubiquitination and/or degradation, and evaluating IAP ubiquitination and/or degradation, wherein diminished ubiquitination and/or degradation of the IAP protein thereby identifies the agent as inhibiting or abrogating apoptosis.

The invention also provides in another embodiment, a method of reducing the severity of a pathologic condition in an individual associated with an abnormal level of apoptosis, comprising the steps of administering to the individual an agent that modulates IAP levels, thereby reducing the severity of the pathologic condition.

RING/+; ubcD1$^{\Delta 73}$/+; G, GMR-Gal4/+; UAS-dronc/+; H, GMR-Gal4/+; UAS-dronc/ubcD1$^{\Delta 73}$. ubcD1 −/+ partially suppresses the eye ablation phenotype of GMR-hid and GMR-rpr (A-D). GMR-diap1-RING induces eye pigment cell death (E). In a ubcD1 −/+ background, pigment loss by GMR-diap1-RING is partially suppressed (F). GMR-dronc similarly induces pigment cell loss (G). However, ubcD1−/+ enhances the effect of GMR-dronc (H). This genetically places ubcD1 downstream of hid, rpr, but not downstream of dronc.

Figure 5:
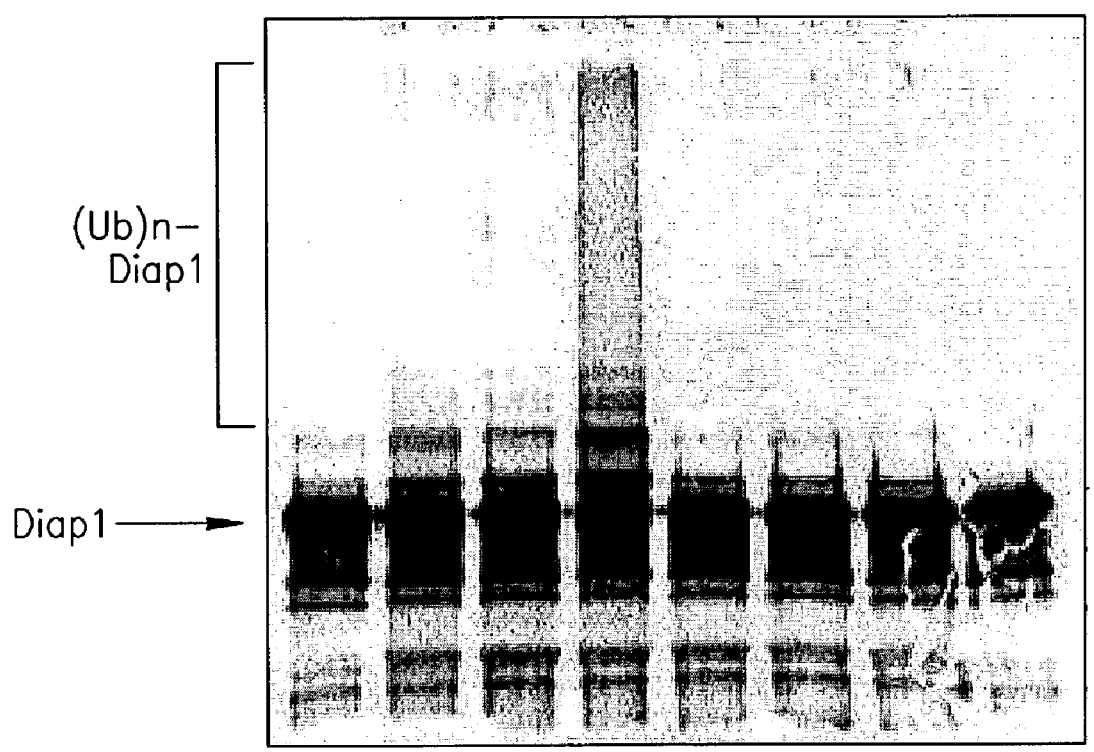

FIG. 5 shows that DIAP1 is a ubiquitin ligase with a self-ubiquitinating activity. In vitro ubiquitination reaction was carried out with in vitro translated $^{35}$S-DIAP1 as described in materials and methods. Lane 1, incubated at 0° C. without E1 and UBCD1. Lane 2, Same as lane 1, but incubated in experimental condition. The purpose of this experiment was to show background activity derived from the reticulocyte lysate extract used to translate the DIAP1. Lane 3, same as Lanes 2, but with E1. Lane 4, same as Lane 3, but with UBCD1. Lane 5-7, same as Lanes 2-4, but with His-DIAP1$^{21-4S}$ mutant (RING domain mutant). Lane 8, as Lane 1, but with His-DIAP1$^{21-4S}$ mutant.

Figure 6:
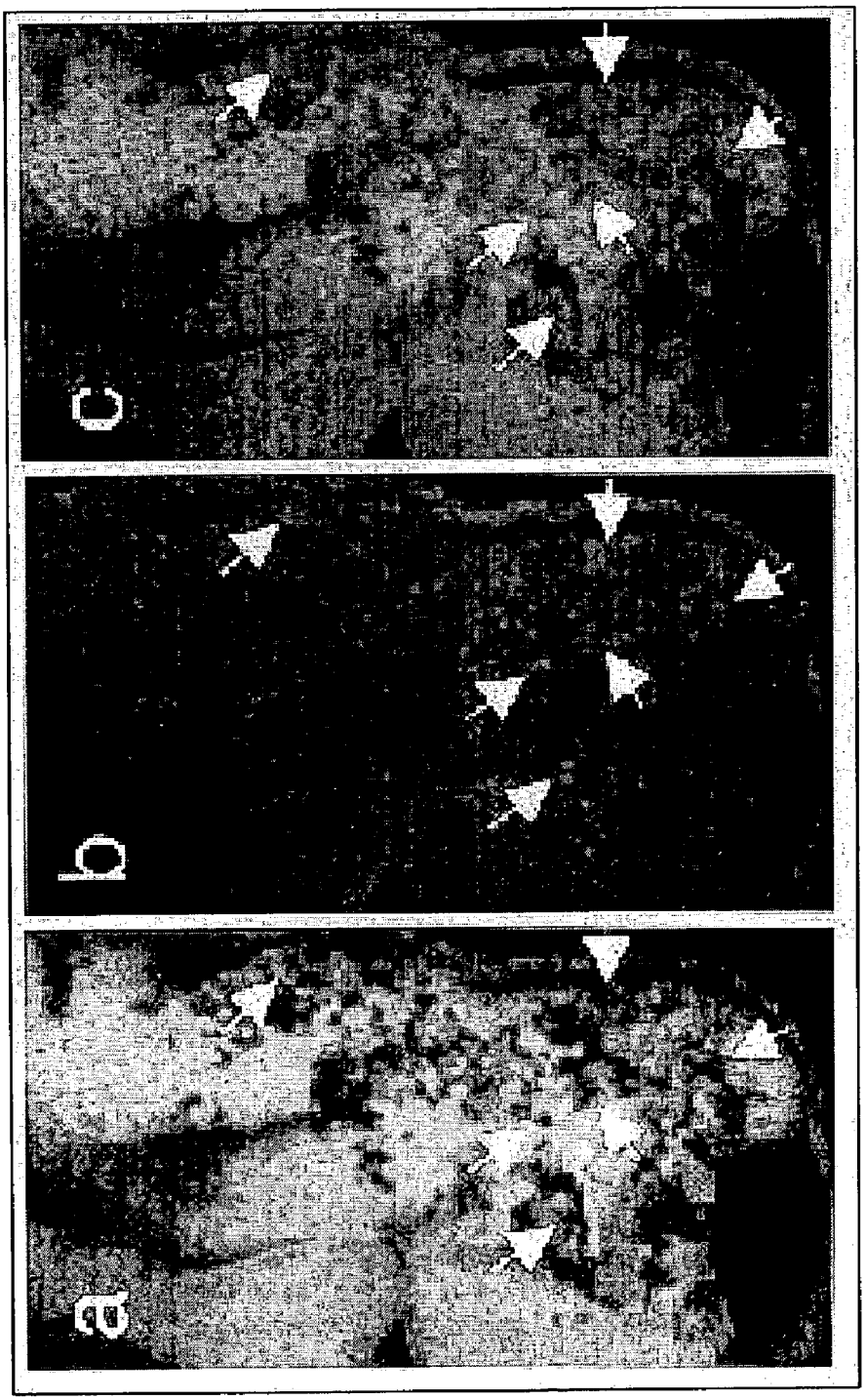

FIG. 6 shows that DIAP1 levels increase in ubcD1 −/− clones. In all panels, arrows point to representative ubcD1 −/− clones that have increased anti-DIAP1 labeling. GFP labeling (light gray) marks wild type chromosomes (A). Cells that are not marked with GFP are ubcD1 −/−. Anti-DIAP1 labeling (dark gray) (B). Merged image of the channels for DIAP1 and GFP labeling (C). All cells that have increased anti-DIAP1 labeling are ubcD1 −/−.

Figure 7:
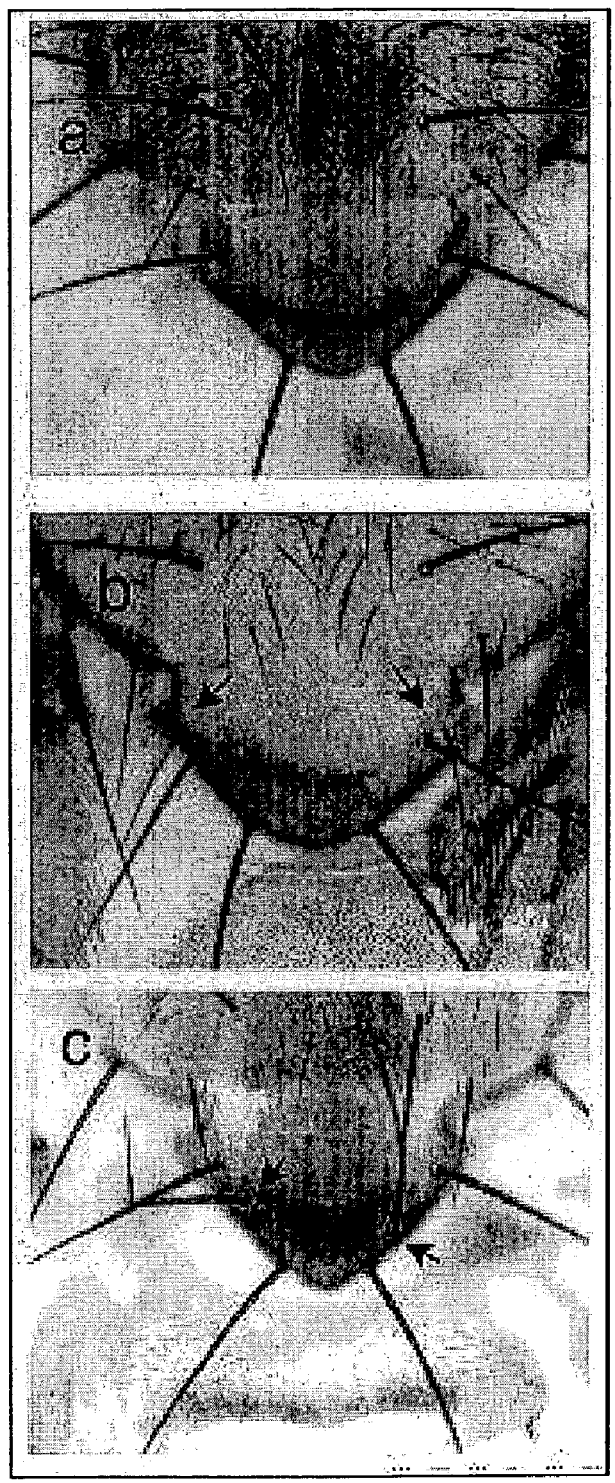

FIG. 7 shows that ubcD1 −/− adults have extra sensory neurons. Canton S (wild type strain) flies invariably have four machrochaetes in the scutellum (A). Expression of the p35 caspase inhibitor leads to extra machrochaetes (arrows) in the scutellum (B). Genotype, UAS-p35; pnr-Gal4. Similarly, trans-heterozygous ubcD1$^{\Delta 112}$/ubcD1$^{\Delta 73}$ adults have extra machrochaetes (arrows) (C).

Figure 8:
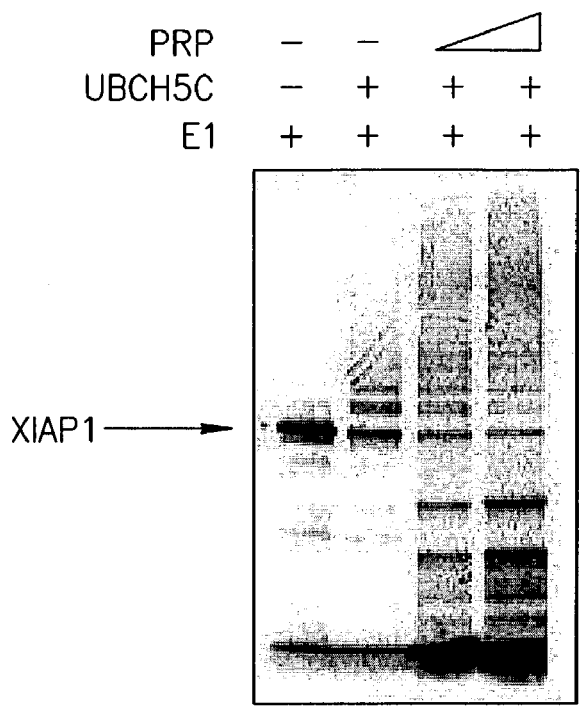

FIG. 8 shows that Reaper strongly stimulates the auto-ubiquitination of human XIAP.

Figure 9:
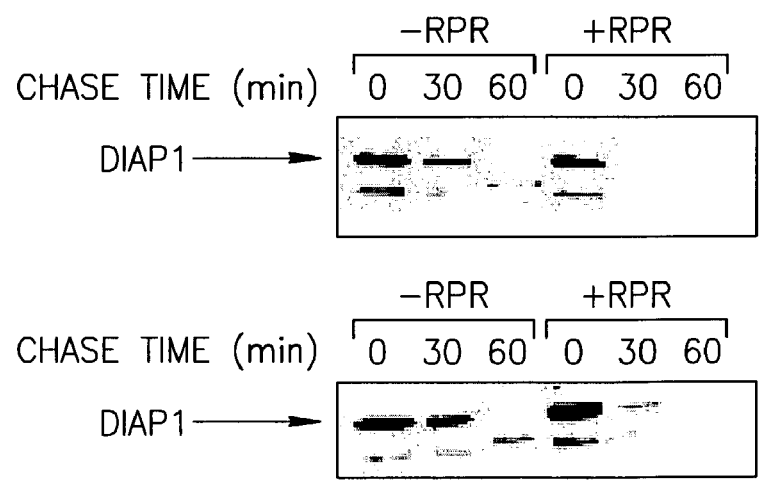

FIG. 9 demonstrates the results of a pulse-chase experiment wherein mammalian cell Reaper expression dramatically shortened the half-live of an IAP (Diap1) protein. Two representative experiments are shown.

FIG. 10 depicts sequence alignments for some of the N-terminal 14 amino acids of the RHG amino acid consensus sequences of the IAPis Reaper, Grim, Hid, Sickle, Smac/Diablo and Omi/HtrA2.

FIG. 11 depicts sequence alignments of the Trp (W) box amino acid consensus sequences of the IAPis Reaper, Grim, and Hid-1-4, revealing a significant number of conserved amino acids among the IAP inhibitors.

FIG. 12 depicts the multiple domains within the Reaper protein, each with a distinct function.

FIG. 13 demonstrates the results of an in vitro self-conjugation assay conducted with Reaper-, Grim- or HID-derived peptides, or wild type Reaper protein. Peptides comprising the N-terminal RHG motif alone did not promote IAP self-conjugation in vitro (A), whereas the addition of the Trp-box motif (B), or the inclusion of wild type Reaper resulted in auto-ubiquitination.

Figure 14:
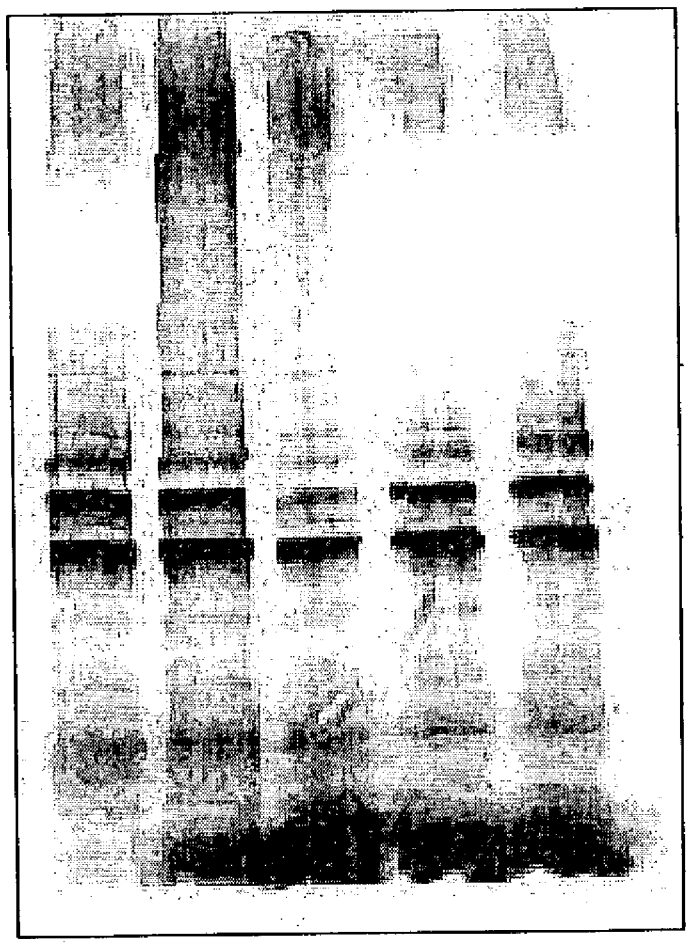

FIG. 14 shows the results of an in vitro self-conjugation assay wherein peptides comprising the Trp box alone failed to stimulate IAP self-conjugation in vitro, in contrast to peptides containing both amino acid consensus sequences, which stimulated self-conjugation.

Figure 15A:
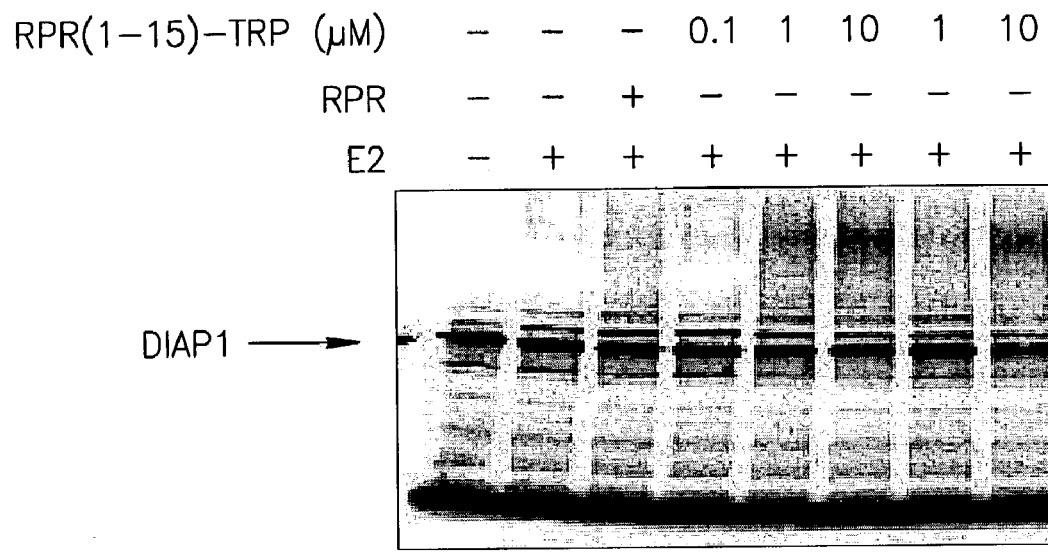
Figure 15B:
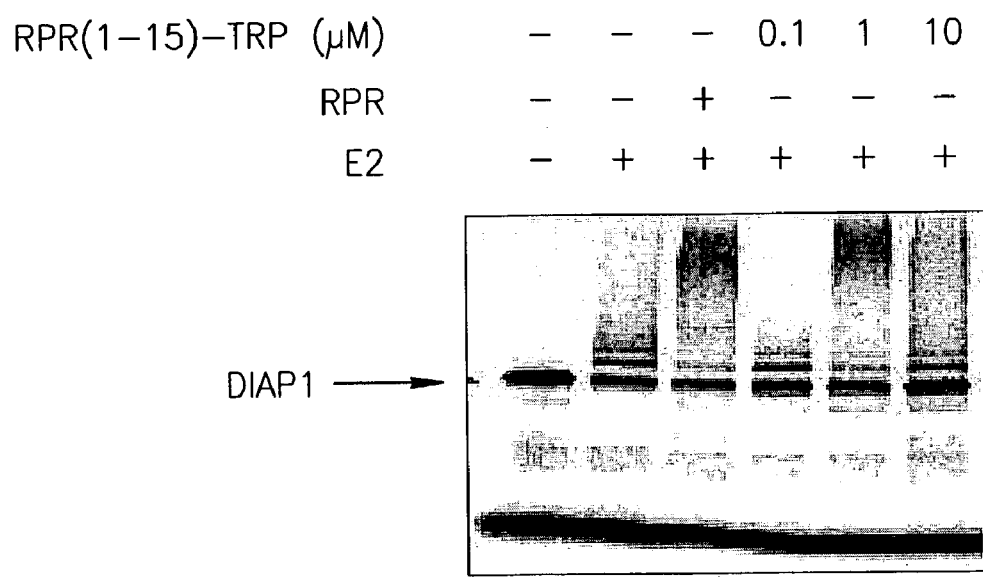

FIG. 15 demonstrates that peptides containing both the RHG-motif and the Trp-box of IAPis can stimulate auto-ubiquitination of Diap1 in vitro (A). Similarly, peptides containing both amino acid consensus sequences function as the wild type Reaper protein in stimulating auto-ubiquitination of XIAP (B).

Figure 16:
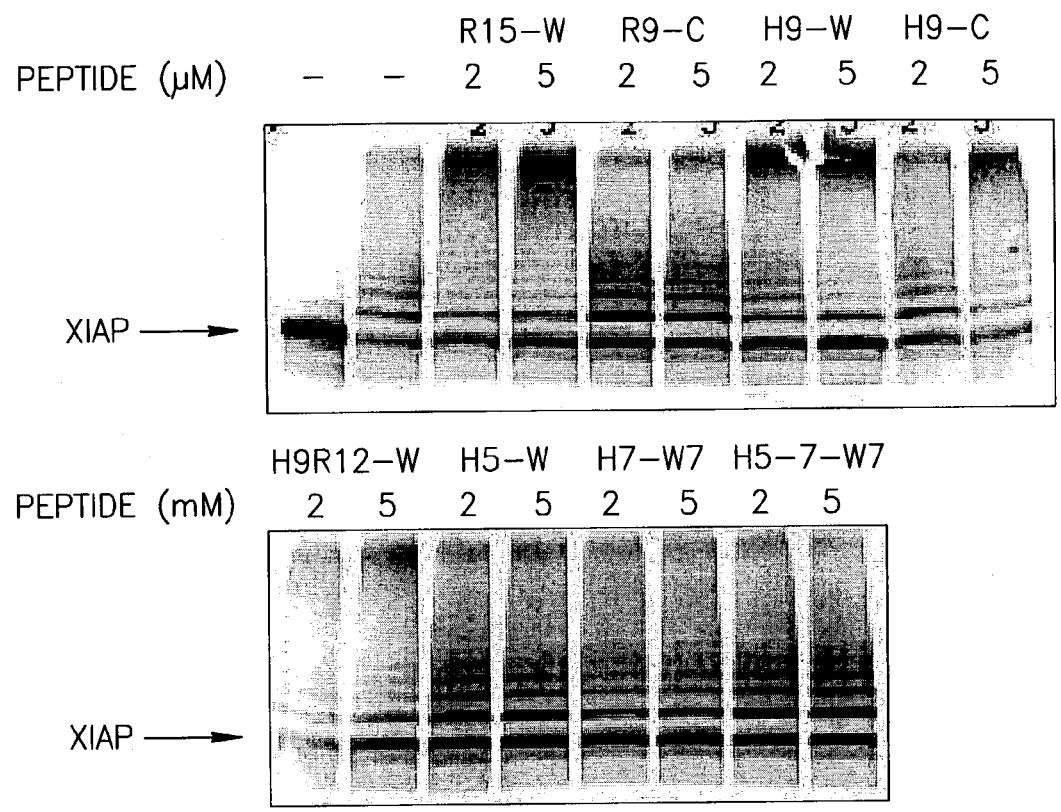

FIG. 16 displays the results of an in vitro XIAP self-conjugation assay. IAPi peptides were generated as described in Table 1, including residues from both RHG-motif and Trp-box amino acid consensus sequences and were assessed for their effect on XIAP self-conjugation (peptide concentrations are as indicated in the figure).

Figure 17:
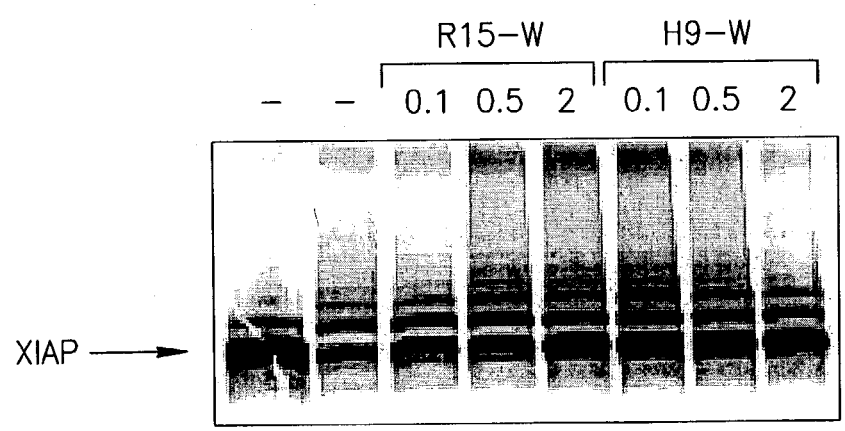

FIG. 17 demonstrates that peptides containing "mixed" IAPi protein amino acid consensus sequences, such as incorporation of a HID-derived RHG-amino acid consensus sequence and an RPR-derived Trp-box, stimulates greater XIAP self-conjugation at nano-molar concentrations than peptides comprising both amino acid consensus sequences derived from Reaper alone.

Figure 18A:
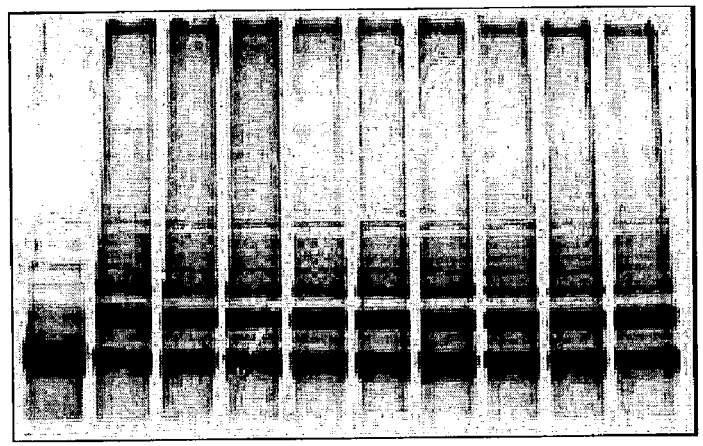
Figure 18B:
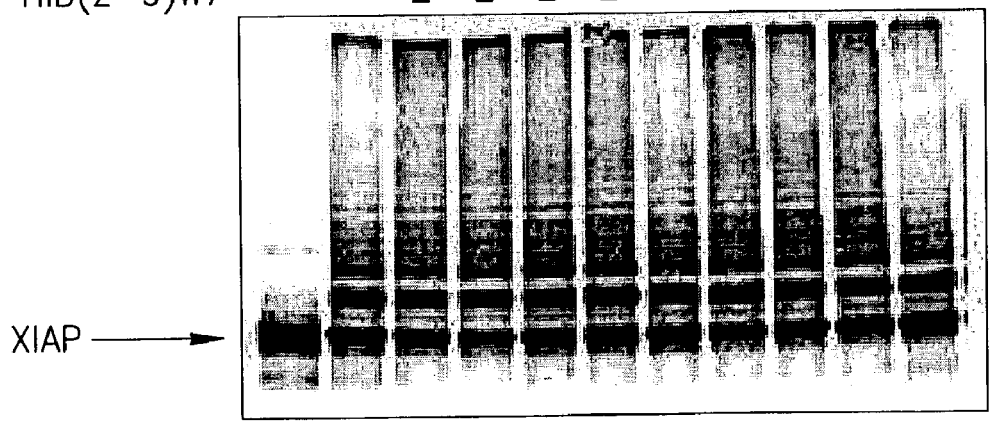

FIG. 18 displays the results of a self-conjugation assay, wherein peptide administration provided either stimulation (FIG. 18A) or inhibition (FIG. 18B) of self-conjugation. Provision of IAPi peptides containing both amino acid consensus sequences, or providing each amino acid consensus sequence in trans was required for XIAP self-conjugation (A). However, addition of excess peptide of either Trp-box or RHG peptides, in conjunction with the stimulating peptide (containing both amino acid consensus sequences) resulted in inhibition of self-conjugation (B).

DETAILED DESCRIPTION OF THE INVENTION

This invention provides novel peptides, nucleic acids, compositions and methods for regulating apoptosis, and therapeutic applications arising from their utilization, in a myriad of pathologies unavailable in the state of the art to date. The invention also provides screening methods for identifying peptides for regulating apoptosis. The following are meant to provide materials, methods, and examples for illustrative purposes as a means of practicing/executing the present invention, and are not intended to be limiting.

In one embodiment, cellular apoptosis is regulated via effecting self-ubiquitination/auto-degradation of an IAP. In another embodiment, apoptosis is regulated via inhibition/downmodulation of self-ubiquitination/auto-degradation of an IAP.

"Cellular apoptosis" is defined herein as a mechanism of programmed cell death, the most common form of physiological (as opposed to pathological) cell death. Apoptosis is an active process requiring metabolic activity by the dying cell; often characterized by shrinkage of the cell, cleavage of the DNA into fragments that give a so-called "laddering pattern" on gels and by condensation and margination of chromatin. Methodology for measuring apoptosis includes, but is not limited to: measurement of DNA fragmentation by pulsed field gel electrophoresis (Belyaev IY and Harms-Ringdahl M., (2002) Radiats Biol Radioecol 42: 279-83) or by terminal deoxynucleotidyl transferase-mediated deoxyuridinetriphosphate nick end-labeling (TUNEL) (Edston E. et al, (2002) Int J Legal Med 116: 22-6), measurement of membrane dielectric changes (Wang X, et al. (2002) Biochim Biophys Acta 1564: 412-20), microscopic examination and confirmation of the presence of characteristic pyknotic nucleii, and others.

One mechanism of regulating cellular apoptosis is via stimulation of the cell death process. It is one object of the present invention to provide a method for stimulating or accelerating cellular apoptosis, the method comprising the step of contacting a cell with an IAP inhibitor (IAPi)-derived peptide, wherein the peptide comprises a Trp-box amino acid consensus sequence or a fragment thereof, and an RHG amino acid consensus sequence or a fragment thereof, of an IAPi protein, thereby stimulating apoptosis.

The term "IAPi" refers to a peptide or protein that inhibits IAP protein function. For example, sickle, a *Drosophila* death gene encodes an IAP-inhibitory protein, that has been shown to relieve caspase inhibition (Srinivasula S M et al (2002) Curr Biol 12(2): 125-30), or the demonstration that HtrA2, a mammalian homologue of the *Escherichia coli* heat shock-inducible protein HtrA, can bind to MIHA/XIAP, MIHB, and baculoviral OpIAP (Verhagen A M, et al (2002) J Biol Chem 277(1): 445-54). Some examples of native IAPis are: REAPER, GRIM, HID, Sickle, Smac/Diablo and Omi/HtrA2.

The term "IAPi-derived" refers to any peptide or peptidomimetic that is naturally or synthetically obtained, exhibiting sufficient homology to active portions of an IAPi molecule, such that IAPi effector function is not compromised. By the term "effector function", it is meant to consider any function, event, downstream effect, etc., which is a direct result of the expression and/or presence of a given molecule. IAPi effector function, in this case refers to any function of an IAPi-derived molecule in regulating apoptosis, which is considered as part of this invention.

The term "homology", as used herein, when in reference to IAPi-derived peptides, indicates a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art.

The term "homology", as used herein, when in reference to polynulcleotides encoding for IAPi-derived peptides, similarly indicates a percentage of nucleotides in a candidate sequence that are identical with the nucleotides of a corresponding native nucleic acid sequence.

Homology may be determined in the latter case by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

An additional means of determining homology is via determination of candidate sequence hybridization, methods of which are well described in the art (See, for example, "Nucleic Acid Hybridization" Hames, B. D., and Higgins S. J., Eds. (1985); Sambrook et al., 1989, Molecular Cloning, A Laboratory Manual, (Volumes 1-3) Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native IAPi peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5× Deinhardt's solution, 10% dextran sulfate, and 20 µg/ml denatured, sheared salmon sperm DNA.

As used herein, the terms "homology", "homologue" or "homologous", in any instance, indicate that the sequence referred to, whether an amino acid sequence, or a nucleic acid sequence, exhibits, in one embodiment at least 70% correspondence with the indicated sequence. In another embodiment, the amino acid sequence or nucleic acid sequence exhibits at least 72% correspondence with the indicated sequence. In another embodiment, the amino acid sequence or nucleic acid sequence exhibits at least 75% correspondence with the indicated sequence. In another embodiment, the amino acid sequence or nucleic acid sequence exhibits at least 80% correspondence with the indicated sequence. In another embodiment, the amino acid sequence or nucleic acid sequence exhibits at least 82% correspondence with the indicated sequence. In another embodiment, the amino acid sequence or nucleic acid sequence exhibits at least 85% correspondence with the indicated sequence. In another embodiment, the amino acid sequence or nucleic acid sequence exhibits at least 87% correspondence with the indicated sequence. In another embodiment, the amino acid sequence or nucleic acid sequence exhibits at least 90% correspondence with the indicated sequence. In another embodiment, the amino acid sequence or nucleic acid sequence exhibits at least 92% correspondence with the indicated sequence. In another embodiment, the amino acid sequence or nucleic acid sequence exhibits at least 95% or more correspondence with the indicated sequence. In another embodiment, the amino acid sequence or nucleic acid sequence exhibits at least 97% correspondence with the indicated sequence. In another embodiment, the amino acid sequence or nucleic acid sequence exhibits at least 99% correspondence with the indicated sequence. In another embodiment, the amino acid sequence or nucleic acid sequence exhibits 95% -100% correspondence with the indicated sequence. Similarly, as used herein, the reference to a correspondence to a particular sequence includes both direct correspondence, as well as homology to that sequence as herein defined.

Homology, as used herein, may refer to sequence identity, or may refer to structural identity, or functional identity. By using the term "homology" and other like forms, it is to be understood that any molecule, whether nucleic acid or peptide, that functions similarly, and/or contains sequence identity, and/or is conserved structurally so that it approximates the reference sequence, is to be considered as part of this invention.

IAPi-derived peptides include, but are not limited to, fragments of native polypeptides from any animal species (including humans), and derivatives of native (human and non-human) polypeptides and their fragments, provided that they have a biological activity in common with a respective native polypeptide. "Fragments" comprise regions within the sequence of a mature native polypeptide. The term "derived" is meant to include amino acid sequence and glycosylation variants, and covalent modifications of a native polypeptide, whereas the term "variant" refers to amino acid sequence and glycosylation variants within this definition. IAPi-derived peptides include all peptides having a qualitative biological activity in common with a native IAPi comprising both REG and Trp-box amino acid consensus sequences, and may, according to additional embodiments of the invention, comprise the entire consensus sequence, or a polypeptide fragment thereof.

It is to be understood that any IAPi-derived peptide of the present invention may be isolated, generated synthetically, obtained via translation of sequences subjected to any mutagenesis technique, as well as obtained via protein evolution techniques, well known to those skilled in the art.

The IAPi-derived molecule interacts with an IAP (inhibitor of apoptosis protein), and in one embodiment of the present invention, and as illustrated in Examples 11 and 12, stimulates IAP auto-ubiquitination and subsequent degradation, such that IAP caspase inhibitory activity is reduced or inhibited, (removing or downmodulating apoptotic inhibition), thereby stimulating or accelerating apoptosis. It is to be understood that by the term "interaction", downstream signaling events resulting in auto-ubiquitination and subsequent degradation, as well as direct physical binding between the IAPi-derived molecule and the IAP are considered as part of the invention.

The caspases are a family of cysteine proteases that cleave C-terminal to an aspartic acid residue in a peptide and are involved in cell death pathways leading to apoptosis (see Martin and Green, Cell 82:349-352 (1995)). The caspases previously were referred to as the "Ice" proteases, based on their homology to the first identified member of the family, the interleukin-1.beta. (IL-1.beta.) converting enzyme (Ice), which converts the inactive 33 kilo Dalton (kDa) form of IL-1.beta. to the active 17.5 kDa form. The Ice protease was found to be homologous to the Caenorhabditis elegans ced-3 gene, which is involved in apoptosis during C. elegans development, and transfection experiments showed that expression of Ice in fibroblasts induced apoptosis in the cells (see Martin and Green, supra, 1995).

Additional peptides sharing homology with Ice and ced-3 have been identified and are referred to as caspases, each caspase being distinguished by a number. For example, the originally identified Ice protease now is referred to as caspase-1, the protease referred to as caspase-3 previously was known variously as CPP32, YAMA, and apopain, and the protease now designated caspase-9 previously was known as Mch6 or ICL-LAP6. The caspase family of proteases are characterized in that each is a cysteine protease that cleaves C-terminal to an aspartic acid residue and each has a conserved active site cysteine comprising generally the amino acid sequence QACXG (SEQ ID NO: 72), where X can be any amino acid and is often arginine.

The IAPs contain a conserved RING finger domain, which functions as an ubiquitin ligase. Ubiquitin ligases, referred to herein also as "E3", recruit E2 ubiquitin conjugating enzymes, such as UbcD1, which get charged with ubiquitin in the presence of and e1 ("ubiquitin carrier") enzyme and ATP. E3 effectively selves as an adaptor between the E2 and a substrate (or target) protein onto which the ubiquitin gets transferred [for a review, see Hershko, A., and Ciechanbover, A. (1998): "The Ubiquitin System", Annu. Rev. Biochem. 67, 425-479], thereby tagging them for proteasome-mediated degradation.

As used herein, the term "E2" refers to ubiquitin-conjugating enzymes, such as UbcD1, which get charged with ubiquitin in the presence of an E1 ("ubiquitin carrier") enzyme and ATP. As used herein, the term "UBCD1" refers to a molecule, which encodes a 147 amino acid ubiquitin-conjugating enzyme similar to mammalian ubcH5 (30-32). IAPs can mediate both self-ubiquitination or caspase ubiquitination.

In one embodiment the IAP subjected to auto-ubiquitination and subsequent self-degradation is DIAP, or a peptide displaying homology to DIAP amino acid sequences, such as those disclosed in NCBI's Entrez protein database, having the Accession numbers: AAC46988, Q24307 or S68452.

In another embodiment, the IAP subjected to auto-ubiquitination and subsequent degradation is human XIAP, or a peptide displaying homology to XIAP amino acid sequences, such as those disclosed in NCBI's Entrez protein database, having the Accession numbers: XP172153, AAL47170, AAL32047 or AAC50373.

In another embodiment, the IAP subjected to auto-ubiquitination and subsequent degradation is Ts-XIAP, or a peptide displaying homology to Ts-XIAP amino acid sequences, such as that disclosed in NCBI's Entrez protein database, having the Accession number: XP172153.

In another embodiment, the IAP subjected to auto-ubiquitination and subsequent degradation are c-IAPs, or a peptide displaying homology to c-IAPs amino acid sequences, such as those disclosed in NCBI's Entrez protein database, having the Accession numbers: Q13490, Q13489, XP040715 or XP040717

In another embodiment, the IAP subjected to auto-ubiquitination and subsequent degradation is NAIP, or a peptide displaying homology to NAIP amino acid sequences, such as those disclosed in NCBI's Entrez protein database, having the Accession numbers: Q9JIB6, Q9JIB3, Q9QUK4, Q9QWK5, Q9R016, Q13075, AAA64504, BAB87181, NP032696, A55478, AAF82752, NP035002, NP035000, NP004527, AAF82751, AAF82749, AAF81198, AAD56765, AAD56764, AAD56763, AAD56761, AAC62265, AAC52045, AAC52047, AAC52977, AAC52976, AAC52975, AAC52974, AAC52973, AAC52972, AAC50371, AAC50372, AAC46988, AAB69223, 2103155A or AAL99667.

In another embodiment, the IAP subjected to auto-ubiquitination and subsequent degradation is ML-IAP, or a peptide displaying homology to ML-IAP amino acid sequences, such as those disclosed in NCBI's Entrez protein database, having the Accession numbers: Q960A5, NP647478 or NP071444.

In another embodiment, the IAP subjected to auto-ubiquitination and subsequent degradation is ILP-2, or a peptide displaying homology to ILP-2 amino acid sequences, such as those disclosed in NCBI's Entrez protein database, having the Accession numbers: Q96P09, Q95M72 or Q95M71.

In another embodiment, the IAP subjected to auto-ubiquitination and subsequent degradation is Apollon, or a peptide displaying homology to Apollon amino acid sequences, such as those disclosed in NCBI's Entrez protein database, having the Accession numbers: AAF75772 or Q9NR09.

In another embodiment, the IAP subjected to auto-ubiqtuitination and subsequent degradation is Survivin, or a peptide displaying homology to Survivin amino acid sequences, such as those disclosed in NCBI's Entrez protein database, having the Accession numbers: AAM44085, AAN76690, BAC22748, NP505949, NP505949, NP660916, NP071610, 1M4MA, O15392, AAK56308, AAK56307, AAG42494, AAM76714, AAH34148 or AAH08718.

IAPi or IAPi-derived molecules mediate IAP auto-ubiquitination and degradation, as demonstrated in Examples 11 and 12, as described hereinbelow. According to one embodiment of the invention, IAPi or IAPi-derived molecules mediate self-ubiquitination and auto-degradation via their E3-stimulating activity, functioning as a ligase for recruiting a ubiquitin-conjugating enzyme molecule, such as UBCD1, which acts as an E2 for IAPs, recruiting ubiquitin to an IAP, and initiating the cascade of events culminating in self-ubiquitination and auto-degradation of an IAP.

As used herein, the term "IAPi" refers to a protein, or a peptide fragment thereof, or a nucleic acid sequence encoding for same, which has a central control function for the regulation of cell death. The term "compound" may be similarly used to indicate any agent that functions as an IAP inhibitor, as described herein. The compound may include a synthetic or natural protein or nucleic acid based molecules. According to one embodiment, the IAPis counteract effector function of IAPs, thereby stimulating/accelerating apoptosis.

IAPi or IAPi-derived molecules mediating IAP auto-ubiquitination and self-degradation, according to one embodiment of the invention, comprise an N-terminal RHG amino acid consensus sequence, or a fragment thereof and a Trp-box amino acid consensus sequence of the IAPi protein, or a fragment thereof.

Several IAPi proteins have been identified, with some corresponding analogs in other species uncovered. IAPi-derived peptides, according to another embodiment, may be derived from any IAPi protein, or a fragment thereof, or a homologue or analog of either the protein or peptide fragment. In one embodiment, the IAPi or IAPi derived peptide displays homology to REAPER amino acid sequences, such as those disclosed in NCBI's Entrez protein database, having the Accession numbers: AAA18983 or Q24475. In another embodiment, the IAPi or IAPi derived peptide displays homology to HID amino acid sequences, such as those disclosed in NCBI's Entrez protein database, having the Accession numbers: AAA79985, AAL55425, Q24106 or NP508454. In another embodiment, the IAPi or IAPi derived peptide displays homology to GRIM amino acid sequences, such as those disclosed in NCBI's Entrez protein database, having the Accession numbers: Q24570, AAG28168, AAG28167 or AAC47727. In another embodiment, the IAPi or IAPi derived peptide displays homology to Smac/Diablo amino acid sequences, such as those disclosed in NCBI's Entrez protein database, having the Accession numbers: Q9NR28, Q9J1Q3, NP620308, NP620307, NP063940, AAG22074, AAF43447 or AAF87716. In another embodiment, the IAPi or IAPi derived peptide displays homology to HtrA2/Omi amino acid sequences, such as those disclosed in NCBI's Entrez protein database, having the Accession numbers: NP713130, NP659540, NP037379, NP062762, Q9J1Y5, O43464, AAC28242 or AAB69763.

As used herein, the term "consensus sequence" refers to an amino acid sequence, which shares high sequence, structural or functional identity among a group of proteins. "RHG amino acid consensus sequence" refers to, in one embodiment, to a 14 amino acid N-terminal motif, corresponding to the formula AIAFFIPDQAXLLX (SEQ ID NO: 64), wherein the consensus is determined when any two amino acid residues are conserved among reaper/hid/grim proteins, and X designates a different sequence among all three proteins. In another embodiment, the RHG amino acid consensus sequence corresponds to a peptide fragment thereof, which is conserved among IAPi proteins.

In another embodiment, the RHG amino acid consensus sequence corresponds to, or is homologous to a peptide fragment, comprising 13 amino acid residues, corresponding to the formula AVPFYLPDQAXLL (SEQ ID NO: 65). In another embodiment, the RHG amino acid consensus sequence corresponds to, or is homologous to a peptide fragment, comprising 11 amino acid residues, corresponding to the formula AVPFYLPDQAX (SEQ ID NO: 66). In another embodiment, the RHG amino acid consensus sequence corresponds to or is homologous to a peptide fragment, comprising 9 amino acid residues, corresponding to the formula AVPFYLPDQ (SEQ ID NO: 73). In another embodiment, the RHG amino acid consensus sequence corresponds to, or is homologous to a peptide fragment, comprising 7 amino acid residues, corresponding to the formula AVPFYLP (SEQ ID NO: 74). In another embodiment, the RHG amino acid consensus sequence corresponds to, or is homologous to a peptide fragment, comprising at least 5 amino acid residues, corresponding to the formula AIAFF (SEQ ID NO: 75). In another embodiment the RHG amino acid consensus sequence corresponds to, or is homologous to a peptide fragment, comprising 2 amino acid residues, corresponding to the formula AI (SEQ ID NO: 76). In another embodiment the RHG amino acid consensus sequence corresponds to, or is homologous to a peptide fragment, comprising 3 amino acid residues, corresponding to the formula AVP (SEQ ID NO: 77) or AIP (SEQ ID NO: 78). In another embodiment, the RHG amino acid consensus sequence corresponds to, or is homologous to a first amino acid residue that is an A, a second amino acid residue that is a V or I, a third amino acid residue that is an A or P, a fourth amino acid that is an F, I, or Y.

It is to be understood that any amino acid sequence whether obtained naturally or synthetically, by any means, exhibiting sequence, structural, or functional homology to the peptides described herein are considered as part of this invention.

The structure of some RHG amino acid consensus sequences of IAPi, or IAPi-derived peptides is further described by the following Table (Table 1), in which Peptide sequence, and corresponding SEQ ID Nos. are indicated. Each peptide sequence listed, in turn, represents an additional embodiment of the invention.

TABLE 1

RHG amino acid consensus sequences of IAPi and IAPi-derived peptides

| IAPi or IAPi-derived Peptide Name | Peptide Sequence | SEQ ID No: |
|---|---|---|
| REAPER | AVAFYIPDQATLLR | 1 |
| HID | AVPFYLPEGGADDV | 2 |
| GRIM | AIAYFIPDQAQLLA | 3 |
| SMAC | AVPIANKSEPHSLSS | 4 |
| DIABOLO | AVPIAQKSEPHSLSN | 5 |
| HtrA2 | AVPSPPPASPRSNYN | 6 |
| Omi | AVPAPPPTSPRSQYN | 7 |
| H2-5 (Hid RHG residues 2-5): | AVPF | 8 |
| H2-7 (Hid RHG residues 2-7): | AVPFYLP | 9 |
| H2-9 (Hid RHG residues 2-9): | AVPFYLPE | 10 |
| H5-7 (Hid RHG residues 5-7): | FYL | 11 |
| R2-9 (reaper RHG residues 2-9): | AVAFYIPD | 12 |

In one embodiment, the RHG amino acid consensus sequence of the IAPi or IAPi-derived peptide is a peptide corresponding to, or, in another embodiment is homologous to SEQ ID Nos: 1, 2, 3, 4, 5, 6, 7, 8, 9, 10, 11, or 12.

Nucleic acid sequences encoding for the RHG amino acid consensus sequence comprise the present invention, as well. As used herein, the term "nucleic acid" refers to polynucleotide or to oligonucleotides such as deoxyribonucleic acid (DNA), and, where appropriate, ribonucleic acid (RNA) or mimetic thereof. The term should also be understood to include, as equivalents, analogs of either RNA or DNA made from nucleotide analogs, and, as applicable to the embodiment being described, single (sense or antisense) and double-stranded polynucleotides. This term includes oligonucleotides composed of naturally occurring nucleobases, sugars and covalent internucleoside (backbone) linkages as well as oligonucleotides having non-naturally-occurring portions, which function similarly. Such modified or substituted oligonucleotides are often preferred over native forms because of desirable properties such as, for example, enhanced cellular uptake, enhanced affinity for nucleic acid target and increased stability in the presence of nucleases.

As will be appreciated by one skilled in the art, a fragment or derivative of a nucleic acid sequence or gene that encodes for a protein or peptide can still function in the same manner as the entire, wild type gene or sequence. Likewise, forms of nucleic acid sequences can have variations as compared to wild type sequences, nevertheless encoding a protein or peptide, or fragments thereof, retaining wild type function exhibiting the same biological effect, despite these variations. Each of these represents a separate embodiment of this present.

The nucleic acids of the present invention can be produced by any synthetic or recombinant process such as is well known in the art. Nucleic acids according to the invention can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences.

DNA according to the invention can also be chemically synthesized by methods known in the art. For example, the DNA can be synthesized chemically from the four nucleotides in whole or in part by methods known in the art. Such methods include those described in Caruthers (1985). DNA can also be synthesized by preparing overlapping double-stranded oligonucleotides, filling in the gaps, and ligating the ends together (see, generally, Sambrook et al. (1989) and Glover et al. (1995)). DNA expressing functional homologs of the protein can be prepared from wild-type DNA by site-directed mutagenesis (see, for example, Zoller et al. (1982); Zoller (1983); and Zoller (1984); McPherson (1991)). The DNA obtained can be amplified by methods known in the art. One suitable method is the polymerase chain reaction (PCR) method described in Saiki et al. (1988), Mullis et al., U.S. Pat. No. 4,683,195, and Sambrook et al. (1989).

In another embodiment, nucleic acid sequences encoding RHG amino acid consensus sequences of an IAPi are provided. Some nucleic acid sequences encoding for IAPi or IAPi-derived RHG amino acid consensus sequences are further described by the following Table (Table 2), in which Genbank accession numbers, polynucleotide coordinates thereof, and corresponding SEQ ID Nos. are indicated. Each of these sequences, in turn, represents an additional embodiment of the invention.

TABLE 2

Nucleic Acid sequences encoding RHG amino acid consensus sequences of IAPi and IAPi-derived peptides:

| SEQ ID No: | Nucleotide sequence: | Corresponding Encoded peptide Name | Peptide SEQ ID No: |
|---|---|---|---|
| 13 | atg gca gtg gca ttc tac ata ccc gat cag gcg act ctg ttg cgg | REAPER | 1 |
| 14 | atg gcc gtg ccc ttt tat ttg ccc gag ggc ggc gcc gat gac gta | HID | 2 |
| 15 | atg gcc atc gcc tat ttc ata ccc gac cag gcc caa ttg ttg gcc | GRIM | 3 |

TABLE 2-continued

Nucleic Acid sequences encoding RHG amino acid consensus sequences of IAPi and IAPi-derived peptides:

| SEQ ID No: | Nucleotide sequence: | Corresponding Encoded peptide Name | Peptide SEQ ID No: |
|---|---|---|---|
| 16 | gcg gtt cct att gca cag aaa tca gag cct cat tcc ctt agt agt | SMAC | 4 |
| 17 | gcg gtt cct att gct cag aaa tcg gag cct cat tct ctc agt aac | Diablo | 5 |
| 18 | gcc gtc cct agc ccg ccg ccc gct tct ccc cgg agt cag tac aac | HtrA2 | 6 |
| 19 | gct gtt cct gct ccg cca ccc act tct ccc cgg agc cag tac aat | Omi | 7 |
| 20 | gcc gtg ccc ttt | H2-5 | 8 |
| 21 | gcc gtg ccc ttt tat ttg | H2-7 | 9 |
| 22 | gcc gtg ccc ttt tat ttg ccc gag | 112-9 | 10 |
| 23 | ttt tat ttg | H5-7 | 11 |
| 24 | gca gtg gca ttc tac ata ccc | R2-9 | 12 |

In another embodiment, the RHG amino acid consensus sequence of the IAPi is encoded by a nucleic acid sequence corresponding to, or, homologous to SEQ ID Nos: 13, 14, 15, 16, 17, 18, 19, 20, 21, 22, 23 or 24.

Methods for modifying nucleic acids to achieve specific purposes are disclosed in the art, for example, in Sambrook et al. (1989). Moreover, the nucleic acid sequences of the invention can include one or more portions of nucleotide sequence that are non-coding for the protein of interest. The invention further provides, DNA sequences which encode proteins similar to those encoded by sequences in Table 2, SEQ ID Nos: 14-26, but which differ in codon sequence due to the degeneracies of the genetic code or allelic variations (naturally-occurring base changes in the species population which may or may not result in an amino acid change), which may encode the proteins of the invention described herein, as well. Variations in the DNA sequences, which are caused by point mutations or by induced modifications (including insertion, deletion, and substitution) to enhance the activity, half-life or production of the polypeptides encoded thereby are also encompassed in the invention.

For effective stimulation or acceleration of apoptosis, IAPi-derived molecules comprise both the RHG amino acid consensus sequence, or a fragment thereof, and a Trp-box amino acid consensus sequence, or a fragment thereof.

The "Trp-box amino acid consensus sequence", as used herein, refers to an amino acid sequence of an IAPi protein, or a peptide derived thereof, which is responsible for IAP self-ubiquitination and subsequent auto-degradation via stimulation of E3 ligase activity of an IAP. The Trp-box amino acid consensus sequences are highly conserved among IAPi proteins, as is demonstrated, for example, in FIG. 11 hereinbelow, indicating an essential function.

The Trp-box amino acid consensus sequences in one embodiment, will comprise between 30-45 amino acid residues of the wild-type IAPi proteins.

In another embodiment, the Trp-box amino acid consensus sequence corresponds to a peptide fragment, comprising 10 amino acid residues, corresponding to or homologous to NWRFLATVVL (SEQ ID NO: 79), or corresponding to or homologous to the formula XXFRLATXXX (SEQ ID NO: 69). In another embodiment the Trp-box amino acid consensus sequence corresponds to a peptide fragment, comprising at least 7 amino acid residues, corresponding to or homologous to NWRFLAT (SEQ ID NO: 80), or corresponding to or homologous to the formula XXRFLAT (SEQ ID NO: 70). In another embodiment the Trp-box amino acid consensus sequence corresponds to a peptide fragment, comprising at least 5 amino acid residues, corresponding to or homologous to RFLAT (SEQ ID NO: 81) or XWXAT (SEQ ID NO: 71). The Trp-box amino acid consensus sequence will comprise at least one Trp amino acid residue between amino acid residues 31-41 or reaper, or 85-95 of grim.

The structure of some Trp-box amino acid consensus sequences of IAPi, or IAPi-derived peptides is further described by the following Table (Table 3), in which peptide sequence, and corresponding SEQ ID Nos. are indicated.

sensus sequences of IAPi, or IAPi-derived peptides are further described by the following Table (Table 4), in which Genbank accession numbers, polynucleotide coordinates thereof, and corresponding SEQ ID Nos. are indicated.

TABLE 4

Nucleic Acid sequences encoding Trp-box amino acid consensus sequences of IAPi and IAPi-derived peptides:

| SEQ ID No: | Nucleotide sequence: | Corresponding Encoded peptide Name | Peptide SEQ ID No: |
|---|---|---|---|
| 30 | cag tgg aga ttc ctg gcc acc gtc gtc ctg | REAPER | 25 |
| 31 | tgc tgg gat ctt ttg gcc cag atc ttg tgc | GRIM | 26 |
| 32 | cag tgg aga ttc ctg gcc acc | HW-7 | 27 |
| 33 | cag tgg aga ttc ctg gcc acc gtc gtc ctg | HW-10 | 28 |
| 34 | cag ttg aga tct tcg tcc acc gtc gtc ctg | R-C | 29 |

In another embodiment, the Trp-box amino acid consensus sequence of the IAPi is encoded by a nucleic acid sequence

TABLE 3

Trp-box amino acid consensus sequences of IAPi and IAPi-derived peptides

| IAPi or LAPi-derived Peptide Name | Peptide Sequence | SEQ ID No: |
|---|---|---|
| REAPER | RLRESQWRFLATVVLETLRQYTSCHPKTGRKSGKY | 25 |
| GRIM | SEFGCWDLLAQIFCYALRIYSYSSSQRQPTVIGISFEIS | 26 |
| HW-7: | QWRFLAT | 27 |
| HW-10: | QWRFLATVVL | 28 |
| R-C (Trp-box control): | QLRSSSTVVL | 29 |

According to another embodiment, the Trp-box amino acid consensus sequence of the IAPi molecule is a peptide which corresponds to, or, is homologous to SEQ ID Nos: 25, 26, 27 or 28.

It is to be understood that proteins and peptides exhibiting peptide sequence homology and/or structural/functional homology to the Trp-box amino acid consensus sequence are to be considered as part of this invention, such that any protein or peptide variant regulating apoptosis via activity consistent with the Trp-box amino acid consensus sequence is envisioned as contained within this invention.

Nucleic acid sequences encoding the Trp-box amino acid consensus sequence comprise the present invention, as well. Nucleic acid sequences encoding Trp-box amino acid concorresponding to, or, in another embodiment homologous to SEQ ID Nos: 30, 31, 32, or 33.

IAPi-derived peptides stimulating/accelerating apoptosis, as is demonstrated in Examples 11 and 12 hereinbelow, comprise both RHG and Trp-box amino acid consensus sequences.

The structure of some IAPi-derived peptides is further described by the following Table (Table 5), in which peptide sequence, RHG and Trp-box amino acid consensus sequence presence, and corresponding SEQ ID Nos. are indicated. These sequences, in turn, represent additional embodiments of the invention.

TABLE 5

Some examples of IAPi-derived peptides

| Peptide Name | Peptide Sequence | Contains RHG amino acid consensus sequence | Contains Trp Box | SEQ ID No: |
|---|---|---|---|---|
| RPR | MAVAFYIPDQATLLRLRESQWRFLATVVLETLRQYTSCHPKTGRKSGKY | + | + | 35 |
| HID | MAVPFYLPEGGADDV LYALYEWVRMYQSQQSAPQIFQYPPPSPSC | + | + | 36 |
| RIM | MAIAYFIPDQAQLLASEFGCWDLLAQIFCYALRIYSYSSSQRQPTVIGISFEIS | + | + | 37 |
| H2-9W7 | AVPFYLP　　　QWRFLAT | + | + | 38 |
| H2-9W10 | AVPFYLP　　　EAAAQWRFLAT | + | + | 39 |
| R15W | AVAFYIPDQATLLR　QWRFLATVVL | + | + | 40 |
| R9-C: | AVAFYIPD　　QLRSSSTVVL | + | − | 41 |
| H9-W: | AVPFYLPE　　QWRFLATVVL | + | + | 42 |
| H9-C: | AVPFYLPE　　QLRSSSTVVL | + | − | 43 |
| H9R12W: | AVPFYLPEQA　TLQWRFLATVVL | + | + | 44 |
| H5-W | AVPF　　　QWRFLATVVL | + | + | 45 |
| H7-W7 | AVPFYLP　　QWRFLAT | + | + | 46 |
| H5-7-W7 | FYL　　　QWRFLAT | + | + | 47 |

In another embodiment, the IAPi-derived peptide stimulating/accelerating apoptosis may comprise "mixed" IAPi amino acid consensus sequences. By the term "mixed", it is meant to include IAPi amino acid consensus sequences, comprised of RHG amino acid consensus sequence derived from one IAPi species, and a Trp-box amino acid consensus sequence derived from a different IAPi species, such as, for example, utilizing the HID RHG amino acid consensus sequence and the RPR Trp-box amino acid consensus sequence, as illustrated in Example 12. Utilization of "mixed" IAPi-derived peptides as such, may provide enhanced stimulation of self-ubiquitination, and stimulation of apoptosis, as is evident in FIG. 17.

It is to be understood that mixed combinations of the two amino acid consensus sequences from any IAPi species are considered as part of this invention.

In another embodiment, the IAPi-derived peptide stimulating/accelerating apoptosis may correspond to the formula: AVPFYLPEXXXQWRFLAT (SEQ ID NO: 61), AVAFYIP-DNXXXXQWRFLATVVL (SEQ ID NO: 62), AVAFYIPD-NXXXQWRFLAT (SEQ ID NO: 63) and AVPFAAARFLAT (SEQ ID NO: 82). In another embodiment, the IAPi-derived peptide stimulating/accelerating apoptosis may comprise 18 amino acid residues, or in another embodiment, the IAPi-derived peptide stimulating/accelerating may comprise 21 amino acid residues. The IAPi-derived peptide stimulating/accelerating apoptosis will comprise, at a minimum, 12 amino acid residues. In additional embodiments, the IAPi-derived peptide stimulating/accelerating apoptosis may comprise between 12 and 15, between 15 and 18, between 18 and 21, between 21 and 25, between 25 and 30, between 30 and 35, between 35 and 40, between 40 and 44, between 44 and 48 or between 48 and 51 amino acid residues.

Protein and/or peptide homology for any peptide sequence listed herein may be determined by immunoblot analysis, or via computer algorithm analysis of amino acid sequences, utilizing any of a number of software packages available, via methods well known to one skilled in the art. Some of these packages may include the FASTA, BLAST, MPsrch or Scanps packages, and may employ the use of the Smith and Waterman algorithms, and/or global/local or BLOCKS alignments for analysis, for example.

Nucleic acid sequences encoding the RHG and Trp-box amino acid consensus sequences comprise the present invention, as well. Nucleic acid sequences encoding RHG and Trp-box amino acid consensus sequences of IAPi, or IAPi-derived peptides are further described by the following Table (Table 6), in which Genbank accession numbers, polynucleotide coordinates thereof, and corresponding SEQ ID Nos. are indicated. These sequences, in turn, represent additional embodiments of the invention.

TABLE 6

Nucleic Acid sequences encoding RHG and Trp-box amino acid consensus sequences of IAPi and IAPi-derived peptides:

| SEQ ID No: | Nucleotide sequence: | Corresponding Encoded peptide Name | Peptide SEQ ID No: |
|---|---|---|---|
| 48 | atg gca gtg gca ttc tac ata ccc gat cag gcg act ctg ttg cgg ttg cgg gag tca cag tgg aga ttc ctg gcc acc gtc gtc ctg gaa acc ctg cgc cag tac act tca tgt cat ccg aag acc gga aga aag tcc ggc aaa tat | RPR | 35 |

TABLE 6-continued

Nucleic Acid sequences encoding RHG and Trp-box amino acid consensus sequences of IAPi and IAPi-derived peptides:

| SEQ ID No: | Nucleotide sequence: | Corresponding Encoded peptide Name | Peptide SEQ ID No: |
|---|---|---|---|
| 49 | atg gcc gtg ccc ttt tat ttg ccc gag ggc ggc gcc gat gac gta cta tac gcc ctc tac gag tgg gtc agg atg tac cag agc cag cag agt gcc ccg caa atc ttc cag tat ccg ccg cca agc ccc tct tgc | HID | 36 |
| 50 | atg gcc atc gcc tat ttc ata ccc gac cag gcc caa ttg ttg gcc tcg gag ttt gga tgc tgg gat ctt ttg gcc cag atc ttg tgc tac gct ctg cga atc tac agc tac agt tcg agc cag cgt caa ccg acg gtc att cag ata tcc ttc gag atc agc | GRIM | 37 |
| 51 | gcc gtg ccc ttt tat H2-9W7 ttg ccc gag ggc cag tgg aga ttc ctg gcc acc | H2-9W7 | 38 |
| 52 | gcn gtn ccn tty tay ytn ccn gar gcn gcn gcn car tgg mgn tty ytn gcn acn | H2-9W10 | 39 |
| 53 | gca gtg gca ttc tac ata ccc gat cag gcg act ctg ttg cgg ttg cag tgg aga ttc ctg gcc acc gtc gtc ctg | R15W | 40 |
| 54 | gca gtg gca ttc tac ata ccc gat cag ttg aga tct tcg tcc acc gtc gtc ctg | R9-C: | 41 |
| 55 | gcc gtg ccc ttt tat ttg ccc gag cag tgg aga ttc ctg gcc acc gtc gtc ctg | H9-W: | 42 |
| 56 | gcc gtg ccc ttt tat ttg ccc gag cag ttg aga tct tcg tcc acc gtc gtc ctg | H9-C: | 43 |
| 57 | gcc gtg ccc ttt tat ttg ccc gag cag gcg act cag tgg aga ttc ctg gcc acc gtc gtc ctg | H9R12-W: | 44 |
| 58 | gcc gtg ccc ttt cag tgg aga ttc ctg gcc acc gtc gtc ctg | H5-W | 45 |
| 59 | gcc gtg ccc ttt tat H7-W7 ttg cag tgg aga ttc ctg gcc acc | H7-W7 | 46 |
| 60 | tat ttg cag tgg aga ttc ctg gcc acc | H5-7-W7 | 47 |

In another embodiment, the IAPi-derived proteins or peptide fragments of the invention directing IAP-dependant regulation of cellular apoptosis are encoded by nucleic acid sequences corresponding to or, in another embodiment, are homologous to SEQ ID Nos: 48, 49, 50, 51, 52, 53, 55, 57, 58, 59 or 60.

In another embodiment of the invention, and as described in Examples 11 and 12 hereinbelow, IAPi engagement of endogenous IAP within a cell promotes self-ubiquitination/auto-degradation of the IAP, and thus the present invention provides a method of inducing self-ubiquitination/autodegradation of an IAP in a given cell. Peptides comprising an RHG and Trp-box amino acid consensus sequence, or peptide fragments thereof are effective in accelerating/stimulating IAP self-ubiquitination/auto-degradation, phenomena, which may readily be measured. Measurements may be conducted through a variety of techniques, well known in the art. For example, self-ubiquitination may be determined in vitro by incubating $^{35}$S-methionine labeled IAp's with a ubiquitin carrier, such as E1 and a ubiquitin ligase enzyme, such as, for example, His-UBCD1 or His-UBCH5C, ubiquitin, ATP, and other necessary components [Ryoo et. al., 2002 Nat. Cell Biol.] as detailed as part of the Materials and Methods section in the Examples section hereinbelow. Imaging of reaction products resolved on a denaturing gel illustrates the presence of self ubiquitination. Another means of determining ubiqulitinlation is via FRET application. Europium cryptate-labeled ubiquitin is used as a fluorescence donor, and streptavidin-labeled allophycocyanin (XL665) as the acceptor. Biotinylated IAP, (XIAP, e.g.) is incubated with streptavidin-labeled XL665, and auto-ubiquitination is determined by measuring fluorescence following the addition of labeled ubiquitin. If the donor and acceptor molecules are brought in close proximity, the fluorescent signal may be resolved with high sensitivity (Nami Yabuki, et al. (1999) Comb. Chem. High Throughput Screen. 5: 279-287), indicating XIAP ubiquitination.

Methods for detection of IAP degradation may comprise measurement of IAP protein expression, including: immunohistochemistry, ELISA, RIA or Western blot analysis [see "Cell Biology: A Laboratory Handbook", Volumes I-III Cellis, J. E., ed. (1994); "Current Protocols in Immunology" Volumes I-III Coligan J. E., ed. (1994); Stites et al. (eds)] for detection of IAP protein expression levels.

The methods rely upon antibody detection of IAPs, some of which are commercially available. Alternatively, and in another embodiment, affinity purified polyclonal antibody against recombinant IAP protein can be generated. Typically, a suitable subject, (e.g., rabbit, goat, mouse or other mammal) is immunized with an IAP immunogenic preparation. An appropriate immunogenic preparation can contain, for example, recombinantly IAP protein or a chemically synthesized IAP polypeptide. The preparation can further include an adjuvant, such as Freund's complete or incomplete adjuvant, or similar immunostimulatory agent. Immunization of a suitable subject with an immunogenic IAP preparation induces a polyclonal anti-DIAP1 antibody response.

The term "antibody" as used herein refers to immunoglobulin molecules and immunologically active portions of immunoglobulin molecules, i.e., molecules that contain an antigen-binding site, which specifically binds an antigen, such as an IAP. A molecule which specifically binds to is a molecule which binds an IAP, but does not substantially bind other molecules in a sample, e.g., a biological sample, which naturally contains an IAP. Examples of immunologically active portions of immunoglobulin molecules include F(ab)

and F(ab').sub.2 fragments which can be generated by treating the antibody with an enzyme such as pepsin.

The present invention provides a means of assessing potential accelerators/stimulators of apoptosis. In another embodiment, there is provided a screening method for potential accelerators/stimulators of apoptosis, comprising the step of contacting a cell with a potential compound and measuring apoptosis in the cell. According to this aspect of the invention, the potential compound may be either an isolated protein, or peptide fragment thereof exhibiting in one embodiment at least 70%, or, in another embodiment at least 72%, or, in another embodiment at leas 75%, or, in another embodiment at least 77%, or, in another embodiment at least 80%, or, in another embodiment at least 82%, or, in another embodiment at least 85%, or, in another embodiment at least 87%, or, in another embodiment at least 90%, or, in another embodiment at least 92%, or, in another embodiment at least 95% or more, including 95%-100% homology to the IAPi-derived peptides, or nucleotides encoding same, as disclosed hereinabove. Compounds for screening mimicking IAPi-derived molecules, as herein described may be generated synthetically, via translation of sequences subjected to any mutagenesis technique, as well as via protein evolution techniques, well known to those skilled in the art.

By the term "contacting a cell", as used herein, it is meant to include any exposure of a cell to a peptide, nucleic acid, or composition of this invention. Cells may be in direct contact with compounds and compositions of the invention, or exposed indirectly, through methods well described in the art. For example, cells grown in media in vitro, wherein the media is supplemented with any of the IAPi-derived peptides, nucleic acids, compounds or compositions would be an example of a method of contacting a cell, considered a part of this invention. Another example would be oral or parenteral administration of a peptide, nucleic acid, compound or composition, whose administration results in vivo cellular exposure to these compounds, within specific sites within a body. Such administration is also considered as part of this invention, as part of what is meant by the phrase "contacting a cell".

In addition to methods for promoting apoptosis and self-ubiquitination of an IAP, the present invention provides compounds and/or compositions for effecting such methods, and as such, represent additional embodiments of the invention.

In one embodiment, apoptosis-promoting/accelerating compounds of the present invention comprise isolated IAPi-derived molecules comprising an N-terminal RHG amino acid consensus sequence and a Trp-box amino acid consensus sequence, or fragments thereof, as described hereinabove.

In another embodiment, there is provided a vector comprising a nucleic acid sequence encoding for IAPi-derived molecules of the present invention.

By "vector" what is meant is a nucleic acid construct containing a sequence of interest that has been subcloned within the vector, in this case, the nucleic acid sequence encoding IAPi-derived molecules. To generate the nucleic acid constructs in the context of the present invention, the polynucleotide segments encoding sequences of interest can be ligated into commercially available expression vector systems suitable for transducing mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter genes.

A vector according to the present invention may include an appropriate selectable marker. The vector may further include an origin of replication, and may be a shuttle vector, which can propagate both in bacteria, such as, for example, E. coli (wherein the vector comprises an appropriate selectable marker and origin of replication) and be compatible for propagation in vertebrate cells, or integration in the genome of an organism of choice. The vector according to this aspect of the present invention can be, for example, a plasmid, a bacmid, a phagemid, a cosmid, a phage, a virus or an artificial chromosome.

The nucleic acid vector may be introduced into desired cells by direct DNA uptake techniques, and virus, plasmid, linear DNA or liposome mediated transduction, receptor-mediated uptake and magnetoporation methods employing calcium-phosphate mediated and DEAE-dextran mediated methods of introduction, electroporation, liposome-mediated transfection, direct injection, and receptor-mediated uptake (for further detail see, for example, "Methods in Enzymology" Vol. 1-317, Academic Press, Current Protocols in Molecular Biology, Ausubel F. M. et al. (eds.) Greene Publishing Associates, (1989) and in Molecular Cloning: A Laboratory Manual, 2nd Edition, Sambrook et al. Cold Spring Harbor Laboratory Press, (1989), or other standard laboratory manuals).

In another embodiment, the present invention provides for a pharmaceutical composition for promoting/accelerating apoptosis, comprising the IAPi-derived molecules described, or vectors expressing same. The presence of both N-terminal RHG amino acid consensus sequence and a Trp-box amino acid consensus sequences, or fragments thereof are required for promoting/accelerating apoptosis, and comprise this aspect of the present invention.

In another embodiment, the vectors may be administered in vitro or ex-vivo, for example, for stimulation of cellular apoptosis. In another embodiment, the compounds may be administered in vitro or ex-vivo, for example, for stimulation of cellular apoptosis. In another embodiment, the compositions may be administered in vitro or ex-vivo, for example, for stimulation of cellular apoptosis. In another embodiment, the vectors/compounds/compositions may be administered in vivo in a number of ways, which are well known in the art. For example, administration may be done topically (including opthalmically, vaginally, rectally, in-tranasally, in the ear), orally, or parenterally, for example by intravenous drip or intraperitoneal, subcutaneous, intracardiac or intramuscular injection.

Compositions may include lotions, ointments, gels, creams, suppositories, drops, liquids, sprays powders or granules, suspensions or solutions in water or non-aqueous media, sachets, capsules or tablets. Thickeners, carriers, buffers, diluents, surface active agents, preservatives, flavorings, dispersing aids, emulsifiers or binders may also be included, all as well other suitable additives, all of which are well known in the art.

Dosing is dependent on the cellular responsiveness to the administered IAPi-derived molecules/compounds or compositions comprising same. Persons of ordinary skill in the art can easily determine optimum dosages, dosing methodologies and repetition rates.

Compounds/compositions comprising IAPi-derived proteins and peptide fragments thereof, and vectors expressing same, provide an enormous reservoir of therapeutic potential for stimulation of apoptosis in cell populations. As just one application of such, it can be envisioned that IAPi-mediated degradation of an IAP can be useful for increasing the level of apoptosis of a population of cells ex vivo, including cells in culture or in an individual.

In another embodiment, a molecule can be used to treat a mixed population of cells in culture, in order to selectively induce apoptosis in one population, thereby facilitating selection of a remaining population. Such a method may entail screening of molecules identified as having pro-apoptotic ability (i.e. they reverse IAP inhibition of caspase activity in a given population), for their ability to be more readily taken up by desired target cell populations. Such methods are well within the level of skill in the art.

Stimulation of apoptosis may be conducted in healthy cells, by the methods disclosed herein, utilizing the aforementioned vectors/compounds/compositions. In another embodiment, the invention provides a method of stimulating apoptosis in a diseased cell. Such stimulation may function as a means of treatment for a given disease, wherein the disease is associated with an abnormally low level of apoptotic cell death. By administering to diseased cells an IAPi-derived molecule, or a pharmaceutical composition comprising an IAPi-derived molecule, IAP auto-degradation is stimulated, thereby accelerating apoptosis.

The cell chosen may be any in which stimulation of apoptosis is desirable. In one embodiment, the diseased cell is a preneoplastic cell, a neoplastic cell, an inflammatory cell or an infected cell. For example, preneoplastic cells in the central nervous system, that fail to undergo apoptosis, yet themselves are not neoplastic, still provide a significant threat to an afflicted host, and selected cellular apoptosis is a therapeutic means of reducing an expanding cell mass in a sensitive anatomic region. Similarly, superantigen engagement of T cell receptors is a mechanism whereby T cell proliferation is enhanced, resulting in autoimmune disease and its associated phenomenon. Selective apoptosis of expanded T cells is a means of controlling T cell proliferation, and downstream effects of such cellular expansion. Selective apoptosis of neoplastic cells causing any of many types of cancer is a well-documented therapeutic approach, with numerous applications well known and investigated in the art [see, for example, Tong Y. et al, Mol Cancer Ther. (2001) 1: 95-102; Mora L. B. et al, Cancer Res. (2002) 62: 6659-66; Opalka B. et al, Cells Tissues Organs. (2002) 172: 126-32]. In addition, undesirable expansion of cell populations occurs in conditions such as psoriasis [Laporte M. et al, Dermatology. (2000) 200: 314-6] and in restenosis [Kolesnick R., J Clin Invest. (2002) 110: 3-8], where such therapeutic intervention would be expected to be highly beneficial. It may also be desirable to target infected cells for apoptosis, prior to cell-to-cell spread a given pathogen. For example, infection with *Mycobacterium tuberculosis* is known to form a single primary focus of infection, where stimulation of apoptosis within the focus may prevent further dissemination and disease.

Similarly, and in other embodiments of the invention, it may be desirable to stimulate apoptosis in cells associated with a neurodegenerative, cardiovascular, inflammatory or autoimmune disease or in infection.

It is to be understood, that any cell whereby stimulation of apoptosis by methods disclosed herein is desired, or via the use of any of the active compounds or compositions herein described, is to be considered as part of the present invention. Diseased cells may in turn comprise cells of hematopoietic, neural or mesenchymal origin, including cells of neuronal, cardiac, muscular, connective, hepatic, osteocytic, adipose, thymic, erythroid, myeloid or epithelial origin.

Another mechanism for regulating cellular apoptosis provided for by the present invention is via suppression of the cell death process. Therefore, in another embodiment of the present invention there is provided a method for inhibiting cellular apoptosis, the method comprising the step of contacting a cell with an IAPi-derived peptide, said peptide comprising a Trp-box amino acid consensus sequence or fragment thereof, or an RHG amino acid consensus sequence or fragment thereof, of an IAPi protein, thereby inhibiting apoptosis. In contrast to the previous peptides, compounds and compositions, stimulating apoptosis, for downmodulation and/or abrogation of apoptosis, IAPi-derived molecules, in one embodiment, will comprise either the RHG or Trp-box amino acid consensus sequence, or may comprise elements of each, yet fails to stimulate auto-ubiquitination, and is another embodiment of this aspect of the invention.

In another embodiment of this invention, a method of downregulating/abrogating apoptosis is provided, comprising contacting a cell with an IAPi-derived peptide, comprising either an RHG amino acid consensus sequence, or a fragment thereof, or a Trp-box amino acid consensus sequence, or a fragment thereof, of an IAPi-derived peptide.

The RHG amino acid consensus sequence according to this aspect of the invention will correspond to, or, in another embodiment, be homologous to SEQ ID Nos: 1, 2, 3, 4, 5, 6, 7, 9, 10, 11, or 12.

In another embodiment, dowregulation/abrogation of apoptosis is via IAPi-derived molecules comprising a Trp-box amino acid consensus sequence corresponding to, or, in another embodiment, be homologous to SEQ ID Nos: 25, 26, 27 or 28.

In another embodiment, downregulation/abrogation of apoptosis is via IAPi-derived molecules comprising an RHG amino acid consensus sequence, or a Trp-box amino acid consensus sequence, encoded by nucleic acid sequences corresponding to or, in another embodiment, homologous to SEQ ID Nos: 13, 14, 15, 16, 17, 18, 19, 20, 21, 22, 23 or 24, or SEQ ID Nos: 30, 31, 32 or 33, respectively.

It is to be understood that this aspect of the invention is in contrast to compounds, compositions and methods utilizing both RHG and Trp-box amino acid consensus sequences, or a fragment thereof comprising elements of both amino acid consensus sequences, which stimulate or accelerate apoptosis, whereas use of either amino acid consensus sequence alone in turn inhibits or abrogates apoptosis.

Apoptosis inhibiting IAPi-derived molecules comprise peptides comprising either one of the amino acid consensus sequences or fragments thereof, or nucleic acid sequences encoding same, as described hereinabove. The IAPi-derived molecule may also be comprised of peptide molecules comprising both amino acid consensus sequences (or nucleic acid sequences encoding same), however, engagement of the BIR amino acid consensus sequence on an IAP, and/or self-ubiquitination of the IAP does not occur, hence apoptosis remains inhibited.

In other embodiments of the invention, according to this aspect of the invention, inhibition of apoptosis may be mediated via IAPi-derived peptides, or polynucleotides encoding same, vectors comprising such polynucleotides, compounds or compositions comprising such peptides or vectors (as described above in reference to IAPi-derived molecules that stimulate apoptosis). According to this aspect of the invention, however, for inhibition of apoptosis, the compounds comprise IAPi-derived molecules that fail to stimulate IAP self-ubiquitination/auto-degradation. The IAPi-derived molecules will comprise, or encode for either the RHG or Trp-box amino acid consensus sequence, or both, consistent with these criteria.

The present invention provides a means of assessing potential downregulators/suppressors of apoptosis. In another embodiment, there is provided a screening method for potential downregulators/suppressors of apoptosis, comprising the step of contacting a cell with a potential compound and measuring apoptosis in the cell. According to this aspect of the invention, the potential compound may be either an isolated protein, or peptide fragment thereof exhibiting, in one embodiment, homology to an IAPi-derived peptide, or nucleotide encoding same, comprising a Trp-box amino acid consensus sequence, or a peptide fragment thereof. Compounds for screening mimicking these IAPi-derived molecules, may be generated synthetically, via translation of sequences subjected to any mutagenesis technique, as well as via protein evolution techniques, well known to those skilled in the art.

In another embodiment, inhibition of apoptosis by methods disclosed above may be conducted in cells that are healthy, or in cells that are diseased.

In another embodiment, IAPi-derived inhibition of apoptosis is conducted in a diseased cell, wherein the disease is associated with abnormally high levels of apoptosis. Cells administered IAPi-derived molecules comprising the N-terminal RHG amino acid consensus sequence or the Trp-box amino acid consensus sequence or fragments thereof, or vectors expressing same, reveal inhibited IAP self-ubiquitination and auto-degradation. IAP self-ubiquitination and auto-degradation according to this aspect of the invention, may be induced by endogenous cellular IAPis. Thus diseased cells with abnormally high expression of IAPis may be treated with IAPi-derived apoptosis inhibitor peptides, vectors encoding same, compounds or compositions, as described, and such administration is considered part of the present invention.

For example, the invention provides methods for treating a diseased cell associated with such pathologic conditions such as neurodegenerative diseases, including Parkinson's disease, Multiple sclerosis, Alzheimer's disease, Huntington's disease, amylotrophic lateral sclerosis (Lou Gehrig's disease), stroke and the encephalopathy associated with acquired immunodeficiency disease (AIDS). Replenishment of nerve cell populations is limited, with diseases resulting in nerve cell death proving an irreversible process. Selective blocking of apoptosis of specific nerve cell populations at risk in a given neurodegenerative disease, may provide a means for control of disease progression.

Other diseased cells associated with abnormally high levels of apoptosis that may be targeted for apoptotic suppression by the IAPi-derived molecules of the present invention comprises for example, cells associated with cardiovascular disease, wherein suppression of apoptosis in cardiocytes following an ischemic event may provide a means of limiting damage associated with myocardial infarctions. Additional diseases associated with abnormally high levels of apoptosis include autoimmune diseases, retinitis pigmentosa and osteoporosis. Cells infected with certain pathogens succumb to high levels of apoptosis, following infection. Some examples are cells infected with HIV, Reovirus, *shigella* and *salmonella*. Suppression of apoptosis in these cells may alter the course of disease, providing a source of therapy for a myriad of diseases associated with high levels of apoptosis.

The present invention provides for the downmodulation/abrogation of apoptosis, via administration of the described IAPi-derived compounds and compositions ex-vivo, in vitro, or in vivo.

IAPi-derived molecules inhibiting IAP degradation may be incubated ex-vivo with target cells in order to decrease the level of apoptosis in the cells. Such a method can be useful, for example, for culturing cells that otherwise undergo apoptosis when placed in culture. Another application may be for treating an individual's cells ex vivo, either to examine the effect of such a treatment on the cells as a prelude to treating the individual in vivo, or as a therapy to the cells themselves, prior to re-administration to the individual. It may also be possible to expand a population of cells via administration of an IAP inhibitor, where administration facilitates continuous proliferation of the cell population, including a population of progenitor or stem cells, which might otherwise undergo apoptosis under similar culture conditions, with the exception of administration of the IAPi.

It is to be understood, that any diseased cell whereby suppression of apoptosis by methods disclosed herein is desired, or via the use of any of the active compounds or compositions herein described, is to be considered as part of the present invention. Cells may in turn comprise cells of hematopoietic, neural or mesenchymal origin, including cells of neuronal, cardiac, muscular, connective, hepatic, osteocytic, adipose, thymic, erythroid, myeloid or epithelial origin.

The invention provides, in another embodiment, a method for reducing the severity of a pathologic condition in an individual associated with an abnormal level of apoptosis, comprising the step of administering an agent that modulates IAP levels or activity to the individual, thereby reducing the severity of the pathologic conditions.

By the term "abnormal level of apoptosis" it is to be understood that increased apoptosis, the presence of apoptosis, decreased apoptosis or the absence of apoptosis, as compared to unafflicted individuals, as a consequence of the pathologic condition, is herein considered, each of which represents an embodiment of the invention.

It is to be understood that the use of the term "modulates" is to refer to stimulating, enhancing, inhibiting or abrogating, as defined herein. Modulating IAP levels refers to IAP expression. In another embodiment, IAP activity is modulated, as described. In another embodiment, effects of IAP expression and/or activity are via IAP ubiquitination and/or degradation.

By the term "reducing the severity of the pathologic condition", it is to be understood that any reduction via the methods, compounds and compositions disclosed herein, is to be considered encompassed by the invention. Reduction in severity, may, in one embodiment comprise enhancement of survival, or in another embodiment, halting disease progression, or in another embodiment, delay in disease progression, or in another embodiment, diminishment of pain, or in another embodiment, delay in disease spread to alternate sites, organs or systems. It is to be understood that any clinically beneficial effect that arises from the methods, compounds and compositions disclosed herein, is to be considered encompassed by the invention.

The identification of modulators of apoptosis thus has enormous clinical significance. It is therefore another object of the invention to provide screening methods for identifying an agent that modulates IAP protein expression levels or activity. The method comprises co-expressing at least one gene coding for the agent in an expression system that allows IAP expression and under conditions, which allow co-expression of the gene, and evaluating the IAP levels and/or activity, wherein modulation of IAP expression and/or activity of the IAP identifies the agent as an IAP modulator.

It is to be understood that IAP modulation is meant to include any IAP, as described herein and to be inclusive of all embodiments described hereinabove. In one embodiment, the expression system is prokaryotic. In another embodiment, the expression system is eucaryotic. In another embodiment, the expression system is in *Drosophila*. In another embodiment, the expression system is mammalian.

Cell based assay systems can be designed to promote IAP expression and co-expression of a candidate agent, with subsequent analysis on IAP protein level expression and/or activity within the cell, or in cell lysates. Such an assay system may be utilized, in another embodiment, as a means of confirming data obtained from cell-free assay systems, or other in vitro assay systems, for identifying candidate modulators of IAP expression and activity.

In another embodiment, cell-free or in vitro systems are utilized for identification of apoptotic modulators. Such systems, in another embodiment, may be automated, to allow for high through-put screening of randomly designed agents in order to identify those agents that effectively modulate IAP protein expression, for example via measuring IAP ubiquitination or degradation.

The terms "agent" or "candidate agent" are to be considered synonymous herein, and represent chemical or biological molecules such as a simple or complex organic molecules, peptides, peptidomimetics, mimetics, proteins, oligonucleotides, nucleic acid, drugs or other compounds.

In one embodiment, the agent is a synthetic peptide, which may contain, for example, amino acids, amino acid equivalents or other non-amino groups or related organic acids such as p-aminobenzoic acid (PABA). In another embodiment, the synthetic peptide may include amino acid analogs having substituted or modified side chains or functional groups. It is to be understood that the synthetic agent, if a peptide, is to be considered in the context of any embodiment for peptides listed herein.

By reference to an agent's ability to "modulate" IAP expression or activity, it is to be understood that the agent may increase or decrease the relative level of degradation of an IAP protein or the relative self-ubiquitination of an IAP, and the level of cellular apoptosis.

In one embodiment IAP ubiquitination or degradation may be determined via numerous in vitro methods, as exemplified herein, and as well known in the art. Downstream effects or IAP degradation, for example, may provide additional means of determining such agent activity, such as via, for example, the measurement of cellular apoptosis or caspase activity, by methods disclosed herein, and via methods well known to those skilled in the art.

The invention also provides for a method of screening for an agent that diminishes or abrogates IAP protein expression or activity, comprising the steps of contacting a candidate agent with an IAP in a system allowing for IAP expression, under conditions which allow for IAP ubiquitination, and evaluating IAP ubiquitination, wherein IAP ubiquitination identifies the agent as one that diminishes or abrogates IAP protein expression or activity. In another embodiment, the agent stimulates IAP degradation.

The invention provides, in another embodiment, a screening method for identification of a candidate agent that stimulates or accelerates apoptosis. The method comprises the steps of co-expressing a gene encoding for the agent in a system enabling IAP co-expression, and evaluating IAP protein expression level and/or activity, wherein any decrease in IAP protein expression level and/or activity is indicative of the agent stimulating or accelerating apoptosis.

In another embodiment, there is provided a screening method for identifying an agent that stimulates or accelerates apoptosis, comprising the steps of contacting a candidate agent with an IAP in a system allowing for IAP expression, under conditions enabling IAP ubiquitination and/or degradation, and evaluating IAP IAP ubiquitination and/or degradation, wherein increased IAP ubiquitination and/or degradation is indicative of the agent stimulating or accelerating apoptosis.

In another embodiment, there is provided a method for identifying an agent that inhibits or abrogates apoptosis, comprising the steps of co-expressing a gene encoding for an agent in a expression system enabling IAP co-expression, and evaluating IAP expression and/or activity, wherein an increase in IAP expression and/or activity identifies the agent as inhibiting or abrogating apoptosis.

In another embodiment, the invention provides a method for identifying an agent that inhibits or abrogates apoptosis, comprising the steps of contacting a candidate agent with an IAP in a system enabling IAP ubiquitination and/or degradation, and evaluating IAP ubiquitination, wherein diminished IAP ubiquitination and/or degradation is indicative of the agent diminishing or abrogating apoptosis.

In another embodiment, the invention provides a method of screening for anti-cancer drugs, comprising the steps of contacting a tumor cell with an agent that induces IAP ubiquitination and/or degradation, wherein IAP ubiquitination and/or degradation is the tumor cells identifies the agent as an anti-cancer drug.

The following examples are intended to illustrate but not limit the present invention.

EXAMPLES

Materials and Experimental Methods

Fly Stocks

The following genotypes were used in this study: For ectopic expression of RPR or hid in the eye, CyO-2xGMR-RPR/Sco[46], GMR-hid10[47] were used. UAS-RPR; UAS-p35 and UAS-hid; UAS-p35 lines were generated by crossing UAS-p35[4], UAS-hid and UAS-RPR[48]. UAS-dronc[34], Pros26[1], pb/TM3[28], st, fafBP/TM6B[29], ubcD2$^{k13206}$/CyO[49], lesswright (lwr)[49], uch-L3[49], ubi 63E[49], ubcD1[59832], ubcD1Δ73[31], ubcD1Δ112[31] were used in the genetic interaction methods, bruce will be described elsewhere (Agapite and Steller unpublished). The w; FRT82B ubcD1Δ73/TM6B line was generated by mitotic recombination. For mosaic analysis of ubcD 1Δ73, ey-flp; FRT82B Ubi-GFP was used. For overexpression analysis, GMR-Gal4, w; en-Gal4, w; prd-Gal4 and pnr-Gal4/TM6B22[50], were used. th$^{j5c8}$ and wg-lacZ were used for gene expression analysis[4,51]. diap1 RING domain mutant alleles are described elsewhere[27]. In brief, diap1$^{33-1S}$ has a premature stop codon after amino acid 350 and lacks the RING domain. diap1$^{22-8S}$ has a Cys to Tyr change at amino acid 415 which is within the RING domain.

Constructs

The constructs diap1-pET14b and ubcD1-pET14b were generated as follows: The full length ORF of diap1 was subcloned into the BamH1 site of pET14b (Novagen) to generate the diap1(WT)-pET14b expression plasmid. For generation of the diap1 mutant, mutant diap1 containing a point mutation converting Cys 406 into Tyr was amplified by RT-PCR from mutant *Drosophila* strain 21-4s, the sequence excised, then subcloned into the BamH1 site of pET14b, to generate the construct diap1$^{21-4S}$pET 14b. For overexpression of ubcD1 in flies, a 9 amino acid Hemagglutinin (HA)-tag was fused C-terminal to the ubcD1 ORF. The HA-tag sequence was TAC CCA TAC GAC GTC CCA GAC TAC GCT TAA (SEQ ID NO: 83). The resulting fusion construct was subcloned into pUAST22 to generate ubcD1-HA-pUAST. Transgenic flies were subsequently generated by germ line transformation of, and overexpression of UBCD 1-HA, which was confirmed via anti-HA antibody staining.

Clonal Analysis and Overexpression in Imaginal Discs

Mitotic recombination was induced in the developing eye imaginal discs using the Flp-FRT method36 and ey-flipase. Gal4/UAS system was used for ectopic expression.

Antibodies, Immunohistochemistry and Western Blots

GST-DIAP16 was expressed in BL21 (pLysS) bacteria, and was gel purified before immunizing rabbits (Cocalico Biologicals). diap1(WT)-pET14b was used to express His-DIAP1 in BL21(pLysS) and was purified according to the manufacturer's protocol (Novagen) and immobilized on nitrocellulose paper to affinity purify anti-DIAP1 antisera. Rabbit anti-β-galactosidase antibody (Cappel, ICN), mouse-anti-β-galactosidase antibody (Sigma), monoclonal anti-Engrailed antibody (Developmental Studies Hybridoma Bank), Rabbit CM1 antibody24 and mouse anti-HA antibody (Babco) were used to stain embryos and imaginal discs under standard conditions. For western blots, 6-18 h hour embryos were homogenized in the lysis buffer (20 mM Tris pH 7.5, 100 mM NaCl, 1% NP-40, 2 mM DTT) and the cell debris was spun down. The supernatant was run on 15% SDS-PAGE gels, transferred to nitrocellulose sheets and probed with Rabbit anti-DIAP1 antibody. Western blot was detected with ECL (Amersham).

Proteins and Peptides:

Amino acid sequences of IAP inhibitor peptides utilized are as indicated in Table 5.

Cellular Stability of DIAP1

Cos-7 cells were transfected with 1 μg of wild-type (wt) Diap1-Flag-pcDNA3 along with 1 μg RPR-HA-pcDNA3 or 1 μg pcDNA3 vector (to maintain an equal amount of DNA in all transfections). Transfections were carried out by using FuGene™. 30 h after transfection, 100 μg cycloheximide (Sigma) was added to each 60 mm dish for 0, 30, 60 min. Cells were harvested and lysed. Equal amount of protein were resolved via SDS-PAGE (10%) and blotted onto nitrocellulose paper. Diap1 was monitored by Western blot analysis using anti-Diap1 antibody and ECL.

Sequence Alignments

The NCBI BLAST was used for sequence analysis.

Antibodies, Immunohistochemistry and Western Blots

GST-DIAP[16] was expressed in BL21 (pLysS) bacteria, and was gel purified prior to rabbit immunization with the construct (Cocalico Biologicals). diap1(WT)-pET14b was used to express His-DIAP1 in BL21(pLysS), was purified according to the manufacturer's protocol (Novagen) and immobilized on nitrocellulose paper for affinity purification of anti-DIAP1 antisera. Rabbit anti-β-galactosidase antibody (Cappel, ICN), mouse-anti-β-galactosidase antibody (Sigma), monoclonal anti-Engrailed antibody (Developmental Studies Hybridoma Bank), Rabbit CM1 antibody[24] and mouse anti-HA antibody (Babco) were used to stain embryos and imaginal discs under standard conditions. For western blots, 6-18 hour embryos were homogenized in lysis buffer (20 mM Tris pH 7.5, 100 mM NaCl, 1% NP-40, 2 mM DTT) and cell debris was removed by centrifugation. The supernatant was run on 15% SDS-PAGE gels, transferred to nitrocellulose sheets and probed with Rabbit anti-DIAP1 antibody. Western blots were detected with ECL (Amersham).

IAP-E2 Binding Assay for Measuring Self-conjugation $^{35}$S-methionine labeled DIAP1 or XIAP was generated in an in vitro transcription-translation system (Promega) from diap1-pET14b and xiap-pcDNA3.1 respectively. For purification of His-UBCD1 and His-UBCH5C, ubcD1-pET14b and ubcH5C-pT7-7 were expressed in BL21 (pLysS) and purified on a Ni-column according to the manufacturer's protocol (Novagen). $^{35}$S-DIAP1 or $^{35}$S-XIAP was incubated with purified UBCD1 or UBCH5C respectively in the absence or presence of the W-7, H2-9 or H2-9W7 peptides. Following incubation of 15 min in room temperature in 20 mM Tris pH7.6, 2 mM DTT, Ni-NTA Agarose beads (Qiagen) were added for additional 30 minutes. The beads were subsequently washed four times with the Tris/DTT buffer, eluted with Laemli buffer and subjected to 10% SDS-PAGE. $^{35}$S-DIAP1 or $^{35}$S-XIAP was visualized by Phosphorimaging.

In vitro Ubiquitination Reaction $^{35}$S-methionine labeled mutant and wild type DIAP1, or wild type XIAP were generated in an in vitro transcription-translation system (Promega) from diap1-pET14b, diap1$^{21-45}$ pET14b and xiap pcDNA3.1 plasmids. For purification of His-UBCD1 and His-UBCH5C, ubcD1-pET14b and ubcH5C-pT7-7 were expressed in BL21 (pLysS) and purified on a Ni-column according to the manufacturer's protocol (Novagen). In vitro ubiquitination assays were carried out in a total volume of 12.5 μl and contained: $^{35}$S-methionine labeled wild type or mutant DIAP1 or Wild type XIAP (approximately 10,000 cpm), and 250ng E1 (made in baculovirus; vector is the kind gift of Dr. Kazuhiro Iwai, University of Osaka, Osaka, Japan). Unless otherwise stated, 1.2 μg His-UBCD1 or His-UBCH5C was used in each reaction. Reaction mixture contained also 40 mM Tris-HCl, pH 7.6, 5 mM $MgCl_2$, 1 mM DTT, 5 μg ubiquitin, 100 ng Ubiquitin-aldehyde, 2 mM ATPγS [Adenosine 5'-O-(3-thiotriphosphate)]. Reactions were incubated for 50 min at 37° C., and resolved, following addition of a sample buffer on SDS-PAGE (10%). Gels were dried and proteins visualized via Phosphorimaging (Fuji, Japan).

Example 1

DIAP1 Expression

Figure 1:
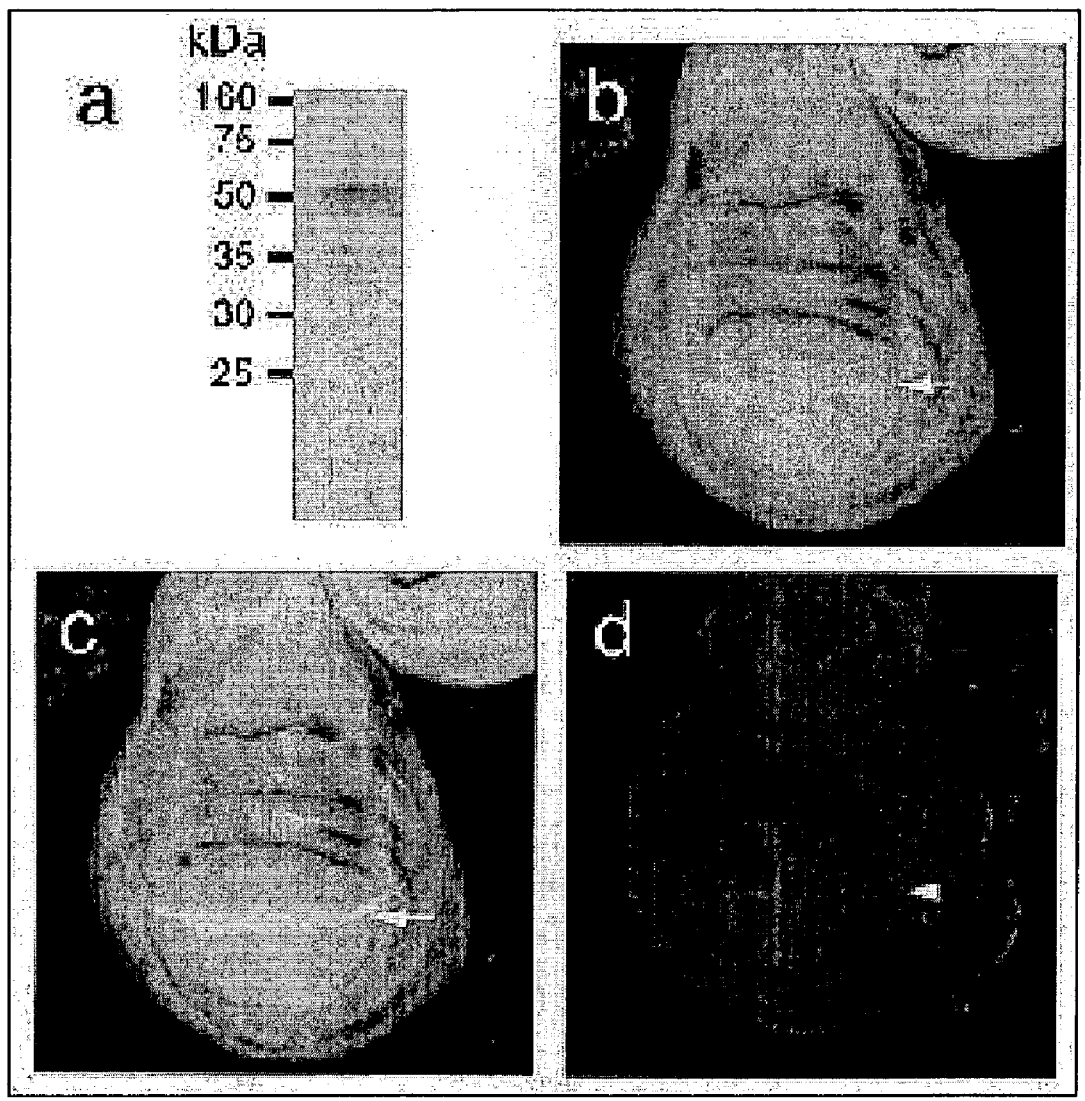
FIG. 1 shows the expression of DIAP1 protein and diap1 enhancer trap in wing imaginal discs. Anti-DIAP1 Western blot of embryo extracts detects a single band of approximately 50 kDa, the predicted size of the diap1 gene product (A). Whole mount anti-DIAP1 labeling of late third instar larval wing imaginal discs, producing a distinctive pattern of anti-DIAP1 labeling (in green) (B,C). The stripe of cells with higher levels of DIAP1 (arrow) coincides with the dorso/ventral (D/V) boundary, as demonstrated by co-staining with the D/V marker wg-lacZ (pale gray). Anti-β-galactosidase labeling (red) of the diap1-lacZ ($th^{j5c8}$) line produces a pattern (D) similar to the anti-DIAP1 labeling in B and C.

In order to investigate how DIAP1 is regulated, it was important to determine DIAP1 expression. An affinity purified anti-DIAP1 polyclonal antibody that detected a single band on western blots (FIG. 1a), was used to probe larval imaginal discs from whole mount tissue. The amount of DIAP1 varied between tissues. Notably, in wing imaginal discs, a stripe of cells showed increased anti-DIAP1 labeling (FIG. 1b). These cells constitute the dorso/ventral (D/V) boundary as demonstrated by double labeling with the wing-less (wg)-lacZ marker (FIG. 1c). Consistent with the anti-DIAP1 antibody labeling pattern, imaginal discs from th$^{j5c8}$ animals, which have a P[lacZ] insertion in the 5' UTR of the diap1 transcription unit[4], showed stronger anti-β-galactosidase labeling along the D/V boundary (FIG. 1d). It is concluded that in the wing imaginal disc, the P[lacZ] reporter expression reflects diap1 transcription.

Unlike neighboring cells of the wing imaginal disc, D/V boundary cells do not proliferate, and thus termed the zone of nonproliferating cells (ZNC)[20]. Since nonproliferating cells are thought to be more resistant to apoptosis during development, transcriptional upregulation of diap1 may confer ZNC a higher threshold to apoptosis during development.

Example 2

RPR Induces Post-transcriptional Downregulation of DIAP1

Figure 2:
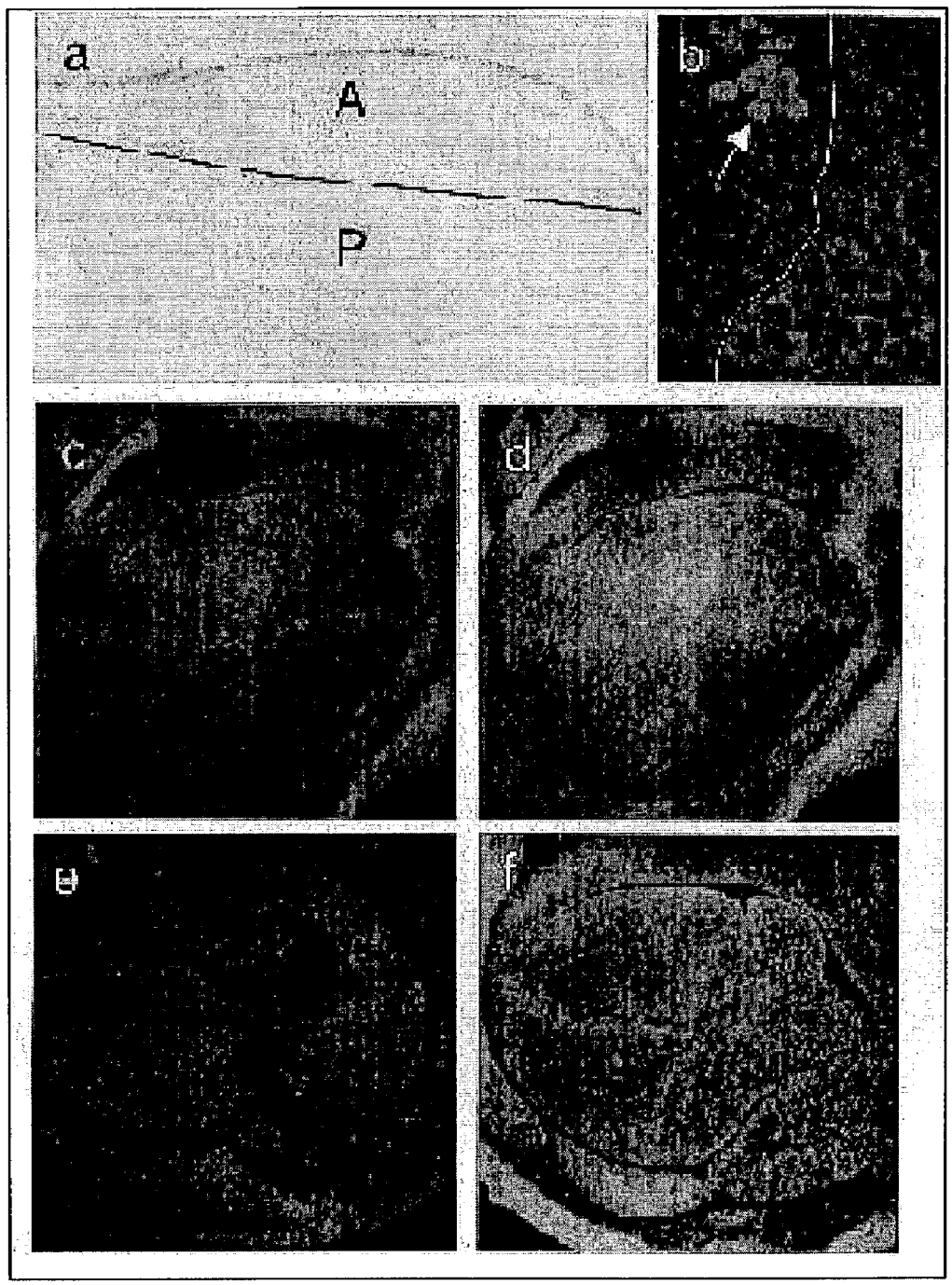
FIG. 2 shows the induction of post-transcriptional down-regulation of DIAP1 by rpr. With the exception of A, anterior is to the left and posterior to the right. Anterior/posterior (A/P) boundary is outlined in A, B and E. A-E, rpr and p35 were ectopically expressed in the wing imaginal disc posterior compartment. Genotype, UAS-rpr; UAS-p35/en-Gal4. p35 completely blocks rpr induced cell death and develops wings indistinguishable from wild type (A). Anterior (A) is up and posterior (P) down. In the anterior compartment, CM1 antibody (light gray) intensely labels naturally dying cells (arrow) (B). In the posterior compartment, all cells are labeled with CM1, but was confined to the cytoplasm. A wing imaginal disc labeled with anti-DIAP1 antibody show reduced DIAP1 levels in the posterior compartment (C, D). Additionally in C, The posterior compartment is marked by double labeling with anti-EN antibody. diap1-lacZ ($thj^{5c8}$) expression (dark gray) is higher in the posterior compartment, indicating that the observed downregulation of DIAP1 in C and D is post-transcriptional (E). hid and p35 were co-expressed in the posterior compartment and labeled with anti-DIAP1 antibody (light gray) (F). Genotype, UAS-hid; UAS-p35/en-Gal4. Compared to C, D, hid induced only a minor reduction of Diap1 labeling.

IAP degradation in thymocytes is a regulated process, wherein glucocorticoids can trigger IAP degradation by unknown mechanisms. To determine whether DIAP1 degradation is also regulated in *Drosophila*, we co-expressed the cell death promoting protein RPR and the baculovirus p35 caspase inhibitor[21] in the wing imaginal disc posterior compartment using the engrailed (en)-Gal4 driver[22]. Expression of p35 prevented RPR-expressing cells from dying, and the resulting cell population not undergoing apoptosis enabled us to observe cellular changes downstream of RPR. Whereas animals expressing RPR alone died as embryos, those co-expressing RPR and p35 survived to adulthood with wings indistinguishable from wild type (FIG. 2a). RPR-induced cell death was completely blocked by p35 as assayed by TUNEL staining of wing imaginal discs. The wing imaginal discs were also labeled with CM1 antibody, which detects activated caspase-3 in humans and cross-reacts with activated caspases in *Drosophila*[23,24]. In the control anterior compartment, sporadic apoptotic cells were intensely labeled with CM1. In contrast, all p35 expressing cells of the posterior compartment showed only low levels of CM1 labeling (FIG. 2b). Whereas the apoptotic cells labeled with CM1 throughout the cell body, p35 expressing cells were labeled with CM1 antibody only in the cytoplasm, indicating that the nuclear membrane was intact and cells were not undergoing apoptosis.

Interestingly, cells expressing both RPR and p35 had reduced anti-DIAP1 labeling as compared to the wild type cells of the anterior compartment (FIG. 2c, d). This reduction in DIAP1 levels was not due to reduced transcription, as diap1-lacZ expression in th$^{j5c8}$ actually increased in these cells (FIG. 2e). Expression of p35 alone did not affect the amount of DIAP1 or diap1-lacZ expression. Since RPR can bind directly to DIAP1[6], these results indicated that RPR/DIAP1 complex formation triggers DIAP1 degradation and occurs independently of caspase activity.

Hid, RPR and grim have different cell killing properties as indicated by their different sets of genetic interactors[7,25,26]. Ectopic hid expression was examined and its effects on DIAP1 expression was determined. When hid and p35 were co-expressed under the en-Gal4 driver, there was only a minor reduction in DIAP1 labeling compared to RPR (FIG. 2f). In addition, there was no increase in diap1-lacZ expression. These data suggested that RHG proteins differ in their ability to promote DIAP1 downregulation.

Example 3

RPR Induces DIAP1 Degradation in a RING Domain Dependent Manner

A number of diap 1 mutant alleles exist that disrupt the RING domain of DIAP1[7,27]. Two such diap1 mutant alleles, diap1$^{33-1S}$ and diap1$^{22-8S}$ were utilized to address the requirement of the RING domain for RPR-dependent DIAP1 degradation.

Figure 3:
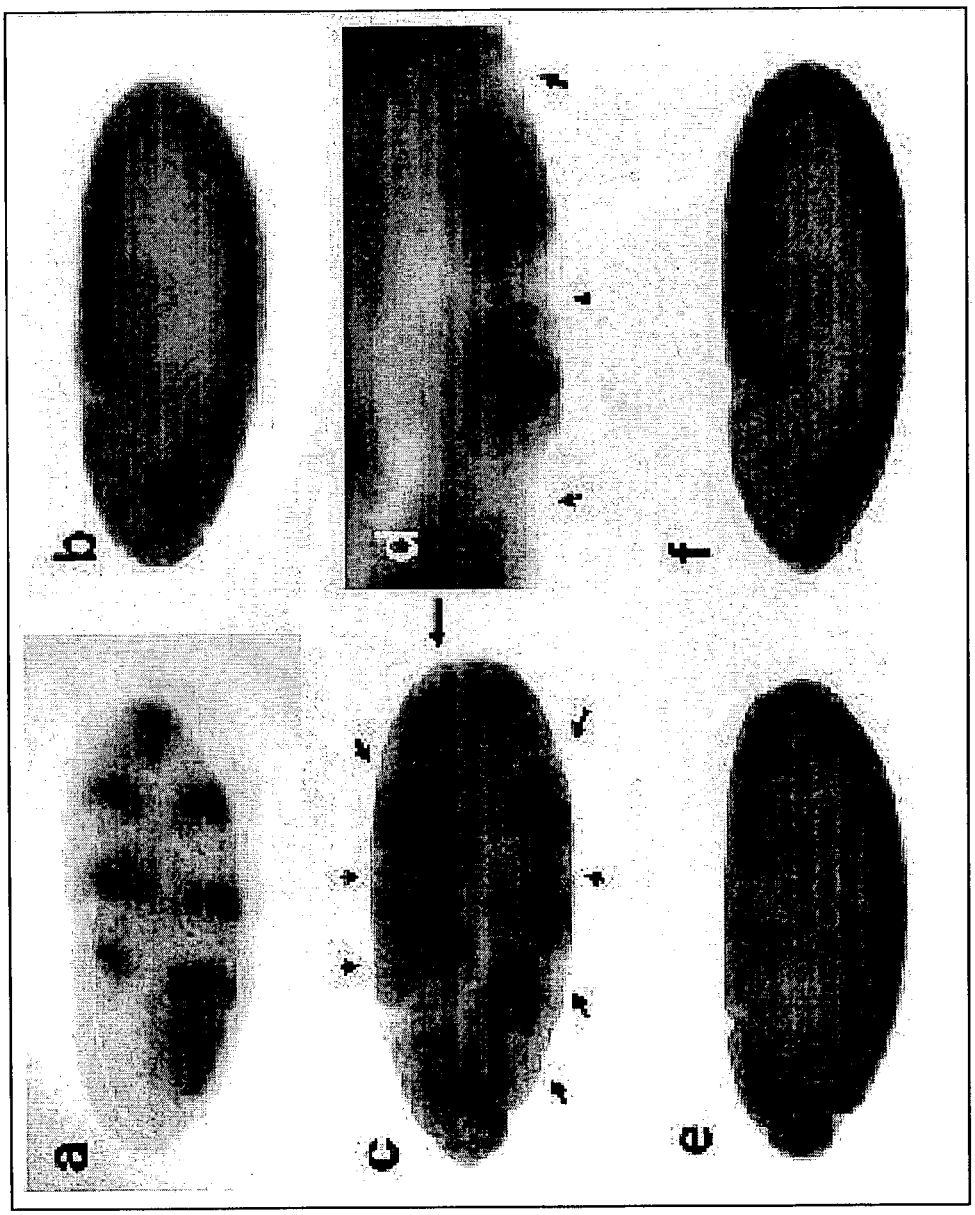
FIG. 3 shows that RPR induced DIAP1 degradation is RING domain dependent. prd-Gal4 expression pattern (A). Genotype, prd-Gal4/UAS-lacZ. Anti-β-galactosidase staining of the embryo shows lacZ expression in a prd-like pattern. Wild type embryo stained with the anti-DIAP1 antibody (B). The DIAP1 protein is homogenously distributed. Expression of rpr reduces DIAP1 staining (C). Genotype, UAS-rpr; prd-Gal4. The domains of rpr expression and of reduced anti-DIAP1 staining match each other (see arrows and compare with embryo in A). Enlarged view of the embryo (D). The degradation of DIAP1 is independent of caspases (E). Genotype, UAS-rpr; UAS-p35; prd-Gal4. Co-expression of the caspase inhibitor p35 does not block rpr induced DIAP1 downregulation. The degradation of DIAP1 in response to rpr expression requires the RING domain (F). Genotype, UAS-rpr; prd-Gal4, $diap1^{33-1S}/diap1^{22-8S}$. Expression of rpr in a RING mutant background fails to trigger DIAP1 degradation.

Homozygous or trans-heterozygous combinations of these alleles are embryonic lethals indicating that the RING domain provides an essential function to DIAP1[7]. Thus, the effect of the RING finger mutations on RPR-dependent DIAP1 degradation in embryos was determined. The protein distribution of DIAP1 was analyzed in embryos that express RPR under the prd-Gal4 driver (FIG. 3a, c). In wild type embryos, DIAP1 is homogenously distributed (FIG. 3b). However, if RPR expression is induced in a prd-like expression pattern, DIAP1 protein levels decrease in exactly those domains where RPR is expressed (FIG. 3c, d). Co-expression of p35 does not affect the decrease of DIAP1 protein levels (FIG. 3e) showing that it occurs upstream of and independent of caspase activation.

To address the importance of the RING domain for DIAP1 downregulation, RPR was expressed in a RING domain mutant background using the diap1$^{33-1S}$ and diap1$^{22-8S}$ alleles. Under this experimental condition, RPR was no longer able to downregulate DIAP1 (FIG. 3f). In conclusion, the reduction of DIAP1 by RPR is due to post-transcriptional regulation, and is mediated via the DIAP1 RIND domain.

Example 4 ubcD1 Promotes RPR and Hid But not Caspase Induced Apoptosis

GMR-hid and GMR-RPR animals ectopically expressed hid or RPR in developing eye discs. Such expression triggers cell killing and is sensitive to the dosage of other cell death related genes, such as diap1[4]. To identify additional factors that regulate DIAP1 self-ubiquitination, we searched animals heterozygous for mutations in the ubiquitin pathway that enhanced or reduced GMR-hid or GMR-RPR induced cell killing (Table 1). Several dominant enhancers of GMR-RPR, including Pros26, a proteasome subunit[28], fat facet, a deubiquitinating enzyme[29] and *Drosophila* bruce, encoding a ubiquitin conjugating enzyme (Agapite and H.S., unpublished) were identified. None of these mutations enhanced GMR-hid induced apoptosis.

Figure 4:
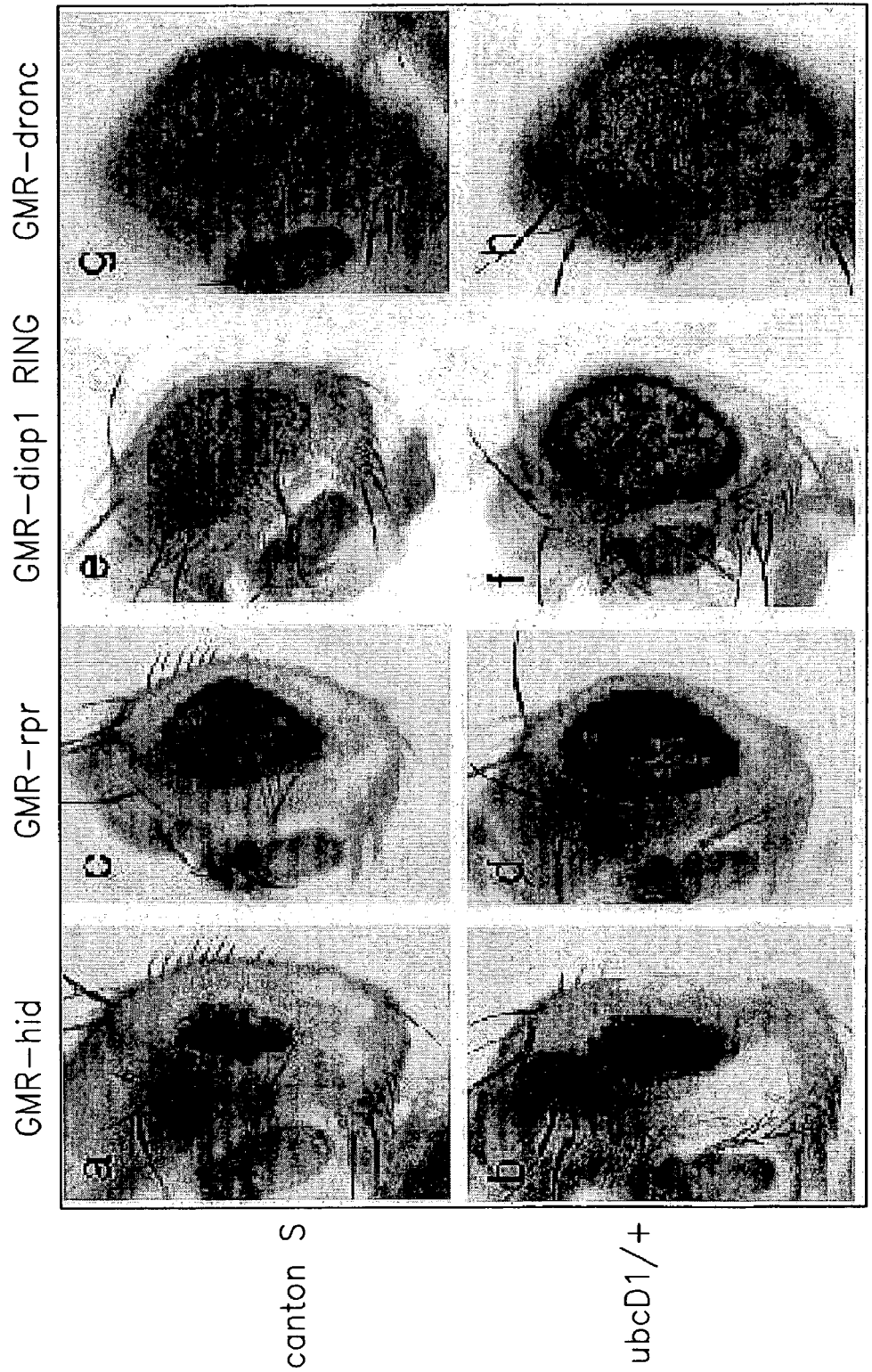
FIG. 4 shows that mutation in ubcD1 dominantly suppresses cell killing induced by GMR-hid, GMR-rpr and GMR-diap1-RING. Cell killing activity as visualized in adult eyes. Genotypes are as follows: A, GMR-hid/+; B, GMR-hid/+; $ubcD1^{\Delta73}$/+; C, GMR-rpr/+; D, GMR-rpr/+; $ubcD1^{\Delta73}$/+; E, GMR-diap1-RING/+; F, GMR-diap1-

Mutations in genes that are required for RPR mediated DIAP1 degradation are expected to dominantly suppress GMR-RPR. Only one such suppressor, ubcD1, also known as effete, was identified. ubcD1 encodes a 147 amino acid ubiquitin conjugating enzyme similar to mammalian ubcH530-32. The dominant suppression of GMR-hid and GMR-RPR was observed with two independent alleles, ubcD1$^{598}$ and ubcD1$^{Δ73}$ (FIG. 4a-d). Interestingly, ubcD1 was previously identified as a genetic interactor of sina, a gene encoding a RING domain-with high sequence similarity to the DIAP1 RING domain[32]. To test if ubcD1 interacted genetically with the RING domain of diap1, ubcD1 flies were crossed to GMR-diap1-RING flies, which overexpress the C-terminal part of DIAP1 including the RING domain. GMR-diap1-RING induced cell death and resulted in small eyes that lacked pigment cells[4] (FIG. 4e). In ubcD1 −/+ animals, the eye phenotype caused by GMR-diap1-RING was suppressed and more pigment cells survived (FIG. 4f).

The dominant suppression of GMR-RPR, GMR-hid and GMR-diap1-RING appears specific to ubcD1, as mutations in lesswright (lwr; a ubc9 homolog) and ubcD2 (a ubc4 homolog) had no effect on GMR-RPR, GMR-hid or GMR-diap1-RING animals (Table 1). ubcD2 has high sequence similarity to ubcD1, and both genes have been shown to functionally substitute for ubc4 in yeast[30,33]. Therefore, these results indicate a striking level of specificity among similar ubiquitin conjugating enzymes in vivo.

hid and RPR induce apoptosis through dronc, a *Drosophila* caspase-9 homolog[34,35]. GMR-dronc induces apoptosis during late pupal stages, which results in loss of pigment cells within normal sized eyes (FIG. 4g). It was found that ubcD1 did not dominantly suppress GMR-dronc, indicating that it acts downstream of RPR, but upstream of dronc (FIG. 4h). In fact, ubcD1 slightly enhanced GMR-dronc, raising the possibility that DRONC may be an additional target for ubcD1-mediated degradation.

DIAP1 is a ubiquitin ligase. In order to determine whether ubcD1 ubiquitin-conjugating function plays a role in DIAP1 degradation, in vitro ubiquitination reactions were conducted (FIG. 5). Wild-type DIAP1 (lane 4) showed marked ubiquitination, whereas the His-DIAP1$^{21-4S}$ mutant (RING domain mutant) did not (lane 7), in the presence of ubcD1.

Taken together, the data demonstrate that UBCD1 functions as an E2 for DIAP1.

Example 5 ubcD1 −/− Cells Exhibit Higher Levels of DIAP1

To further confirm the role of ubcD1 in DIAP1 degradation, we generated mosaic animals with ubcD1 −/− cells in the context of a largely ubcD1 −/+ animal using the Flipase/FRT system[36]. Flipase driven with the eyeless promoter (ey-flp) created small ubcD1 −/− clones in eye imaginal discs, which were marked by the absence of GFP expressed from wild type chromosomes. A subset of ubcD1 −/− cells labeled stronger with anti-DIAP1 antibody, whereas wild type cells never had elevated DIAP1 labeling (FIG. 6). This is consistent with the role of ubcD1 in promoting DIAP1 degradation.

Example 6

Extra Cells are Observed in ubcD1 −− Adults

Each *Drosophila* sensory hair (macrochaete) represents a sensory neuron. *Drosophila* adults show an invariant pattern of sensory cells in the thorax, with four macrochaetes in the scutellum (FIG. 7a). Therefore, the number of macrochaetes has been used as an indicator for defects in cell death or survival[37,38]. Control of apoptosis partly contributes in regulating the number of macrochaetes, since expression of p35 with panier (pnr)-Gal4 driver leads to extra macrochaetes in 30% of animals (N=39) (FIG. 7b). UAS-bcl-238 crossed to pnr-Gal4 produced similar results (data not shown). Neither of the two parent lines, pnr-Gal4 nor UAS-p35, gave extra macrochaetes.

Viable adults were obtained with a trans-heteroallelic combination of ubcD1Δ73/ubcD1Δ112, albeit with low penetrance. Interestingly, 21% of the surviving adults had extra macrochaete (N=49) similar to UAS-p35; pnr-Gal4 adults (FIG. 7c). Examination of ubcD1598/ubcD1Δ112 adults gave similar results. These results demonstrate that ubcD1 affects the number of macrochaetes in adults, and are consistent with a role for ubcD1 in apoptosis.

Example 7 ubcD1 Alone is not Sufficient to Promote DIAP1 Degradation

To test if overexpression of ubcD1 is sufficient to promote DIAP1 degradation, the en-Gal4/UAS-ubcD1 animals were analyzed wherein UbcD1 was ectopically expressed in posterior compartments. There were no signs of any developmental abnormalities in these larvae as examined during late third instar larval stage. DIAP1 protein level remained unchanged in cells expressing UbcD1, as compared to its neighboring control cells of the anterior compartment. In conclusion, ubcD1 is not sufficient to promote DIAP1 degradation when expressed alone and additional factors such as RPR are required in order to ubiquitinate DIAP1 in vivo.

The above Examples demonstrated that RPR promoted significant DIAP1 degradation. RPR-mediated DIAP1 degradation is likely to be upstream of caspase activation, as blocking caspases with p35 maintained RPR's ability to downregulate DIAP. Also, we demonstrate that the DIAP1 RING domain is essential for DIAP1 degradation in vivo. UBCD1, an E2 ubiquitin-conjugating enzyme genetically interacts with DIAP1. Moreover, UBCD1 promotes DIAP1 ubiquitination in vitro. Based on these results, the simplest model is that RPR binding to DIAP1 promotes ubiquitination of DIAP1 via UBCD1. Surprisingly, ectopic hid expression produced only a minor effect on DIAP1 levels. Interestingly, DIAP1 subcellular distribution appeared to be modified by hid. Our observations demonstrated that RPR differentially regulates DIAP1 expression, as compared to HID, in the systems examined.

ubcD1-mediated DIAP1 degradation is highly specific. Three other ubiquitin conjugating enzyme mutants did not suppress apoptosis (Table 1). Notably, ubcD2, encoding a ubiquitin conjugating enzyme with high sequence homology to ubcD133, did not score in the genetic interaction assay with GMR-RPR or GMR-hid. Furthermore, mutation in another ubiquitin conjugating enzyme, bruce, dominantly enhanced GMR-RPR induced cell death (Agapite and H.S., unpublished). Taken together, the results indicated that other apoptotic molecules are likely to be targets of ubiquitination by DIAP1. Furthermore, DIAP1 pairs with a specific ubiquitin-conjugating enzymes to target a different set of molecules for ubiquitination.

TABLE 1

Genetic interaction assay with GMR-hid and GMR-RPR.

No modification:

ubcD2 (ubc4 homolog), lesswright (ubc9), ubi 63E (ubiquitin), uch-L3 (deubiquitinating enzyme), seven in absentia (sina)

Enhancer of GMR-RPR:

Pros26 (Proteasome subunit), fat facet (deubiquitinating enzyme), bruce (mod86)

Suppressor of GMR-hid, GMR-RPR:

ubcD1 (alleles Δ73 and 598)

Individual mutants were crossed to either GMR-hid or GMR-RPR, and their progeny were compared to unmodified GMR-hid or GMR-RPR. For unmodified controls, GMR-hid or GMR-RPR were outcrossed to canton S.

Example 8

Reaper Strongly Stimulates the Auto-ubiquitination of Human XIAP

Reaper activity effects human XIAP self-ubiquitination as well. As is evident from FIG. 8, Reaper strongly stimulated auto-ubiquitination of human XIAP. Thus Reaper proteins stimulate autoubiquitination of IAP proteins.

Example 9

Expression of Reaper in Mammalian Cells Dramatically Shortens the half-live of an IAP (Diap1) Protein In order to determine the effect of the IAP inhibitor (IAPi), Reaper's expression on IAP protein stability, a pulse-chase experiment was conducted using Cos-7 cells co-transfected with Diap1-Flag-pcDNA3 and RPR-HA-pcDNA3 or pcDNA3 vector alone treated with cycloheximide for 0, 30 or 60 minutes, followed by cell lysis, and immunoblot analysis. As is evident from FIG. 9, while cells lacking reaper expression reveal significant IAP protein levels following the 30 minute chase period, Reaper protein expression resulted in a dramatic reduction in detectable IAP protein, reflective of a diminished half-life.

Example 10

Characterization of the N-terminal RHG Amino Acid Consensus sequence and the Trp-box Amino Acid Consensus Sequence of the REAPER Protein In order to further characterize functional amino acid consensus sequences within Reaper and similar IAPis that may be responsible for altering IAP protein stability, a variety of sequence alignments were performed. Protein sequences of IAPis Reaper, Grim, Hid, Sickle, Smac/Diablo and Omi/HtrA2 were aligned, and a 14 amino acid N-terminal peptide motif (RHG motif) was found to be highly conserved (FIG. 10). In addition, the presence of Trp (W) boxes, which participate in IAP ubiquitination activity, was investigated in the IAPis in order to further address their role in altering IAP protein stability. As is evident in FIG. 11, the Trp boxes are highly conserved among the IAPi proteins. Based on these findings, it was hypothesized that the IAPis, and Reaper in particular contain 2 distinct amino acid consensus sequences responsible for IAP degradation, an RHG amino acid consensus sequence which is responsible for binding the BIR amino acid consensus sequence of an IAP, and a Trp box which stimulates IAP auto-ubiquitination (FIG. 12).

Example 11

Figure 13A:
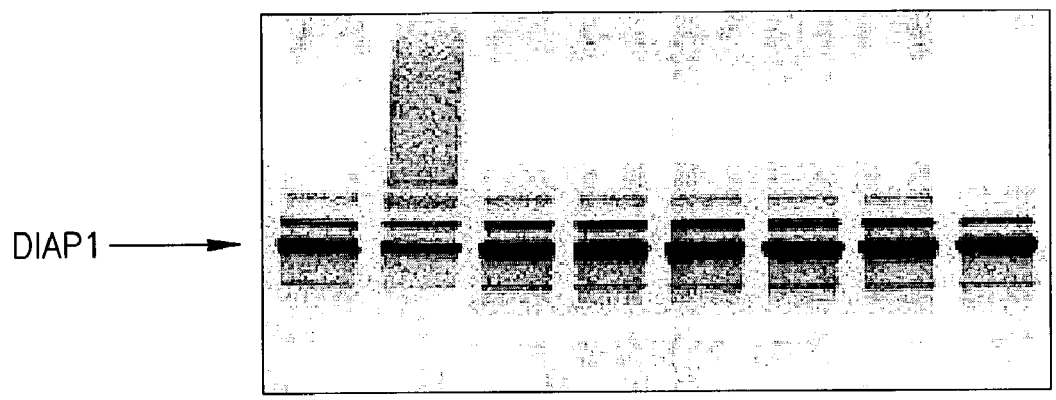
Figure 13B:
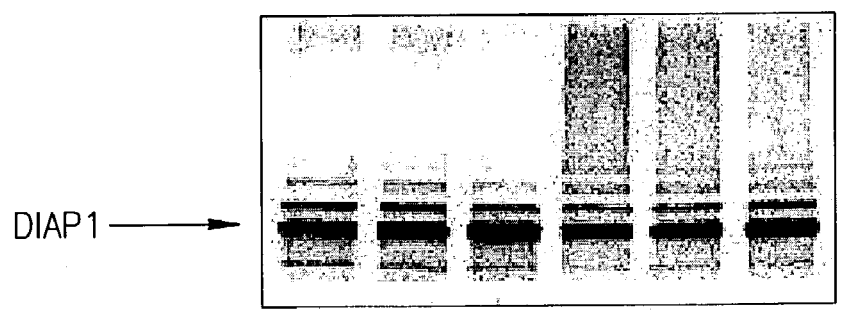

Both N-Terminal RHG Motif and the Trp-box Motif are Necessary for IAP Auto-ubiquitination and Self-conjugation In order to determine whether both amino acid consensus sequences described above are essential for IAP degradation, peptides were generated, with amino acid sequences as described in Tables 1, 3 and 5 above, containing one of each amino acid consensus sequence, or both, and their ability to stimulate in vitro IAP ubiquitination was assessed (FIG. 13). $^{35}$S-methionine labeled wild type DIAP1 was incubated with 250 ng E1 and ubiquitin, with or without the addition of the RPR wild type protein, or peptides containing the RHG amino acid consensus sequence of the RPR HID or GRIM proteins, and the reaction products were resolved by SDS-PAGE. As is evident from FIG. 13A, peptides containing the N-terminal RHG motif alone do not promote IAP self-conjugation in vitro, but peptides comprising both motifs stimulated IAP ubiquitination. Similarly, peptides comprising the RHG amino acid consensus sequence of GRIM alone do not promote IAP ubiquitination, as compared to peptides containing both amino acid consensus sequences (FIG. 13B).

Just as the RHG amino acid consensus sequence alone is insufficient to stimulate IAP ubiquitination, the Trp box amino acid consensus sequence alone is also insufficient in stimulating IAP ubiquitination (FIG. 14). IAP self-conjugation and ubiquitination did not occur when Trp box peptides were utilized, however the use of HID-derived peptides from both amino acid consensus sequences stimulated IAP ubiquitination.

Example 12

Peptides Containing the RHG-motif and the Trp-box can Stimulate auto-ubiquitination of Both Diap1 and XIAP Peptides containing the RHG-motif and the Trp-box can stimulate ubiquitination of both Diap1 (FIG. 15A) and XIAP (FIG. 15B) in vitro, as compared to negative controls. Similarly, peptides containing both motifs are efficient in stimulating XIAP self-conjugation in vitro (FIG. 16). While all peptides demonstrated an ability to induce self-conjugation of XIAP, the IAPi peptides R15W and H9-W revealed the greatest effect, under the experimental conditions examined.

Amino acid consensus sequences derived from Reaper stimulate effective XIAP self-conjugation, yet "mixed" peptides containing the RHG amino acid consensus sequence of the HID protein, with the Trp box of the RPR protein provided greater levels of self-conjugation, effective at a lower concentrations than peptides derived from Reaper alone (FIG. 17).

Example 13

Inhibition of Self-conjugation by Trp-box or RHG Peptides

While addition of peptides containing both amino acid consensus sequences of the IAPis promote IAP self-conjugation, leading to its degradation and promoting apoptosis (FIG. 18A), competitive inhibition may be achieved via the addition of an excess of peptide comprising either of the two amino acid consensus sequences (FIG. 18B).

References (other references included in text):

1. Jacobson, M. D., Weil, M. & Raff, M. C. Programmed cell death in animal development. *Cell* 88, 347-354 (1997).
2. Hengartner, M. O. The biochemistry of apoptosis. *Nature* 407, 685-687 (2000)
3. Goyal, L. Cell death inhibition: keeping caspases in check *Cell* 104, 805-808 (2001).
4. Hay, B. A., Wassarman, D. A. & Rubin, G. M. *Drosophila* homologs of baculovirus inhibitor of apoptosis proteins function to block cell death. *Cell* 83,1253-1262 (1995).
5. Wang, S. L., Hawkins, C. J., Yoo, S. J., Muller, H. A. & Hay, B. A. The *Drosophila* caspase inhibitor DIAP1 is essential for cell survival and is negatively regulated by HID. *Cell* 98, 453-463 (1999).
6. Goyal, L., McCall, K., Agapite, J., Hartwieg, E. & Steller, H. Induction of apoptosis by *Drosophila* reaper, hid and grim through inhibition of IAP function. *EMBO J.* 19, 589-597 (2000).
7. Lisi, S., Mazzon, I. & White, K. Diverse domains of THREAD/DIAP1 are required to inhibit apoptosis induced by REAPER and HID in *Drosophila*. *Genetics* 154, 669-678 (2000).
8. Wu, J. W., Cocina, A. E., Chai, J., Hay, B. A. & Shi, Y. Structural analysis of a functional DIAP1 fragment bound to grim and hid peptides. *Mol. Cell* 8, 95-104 (2001).
9. White, K., Grether, M. E., Abrams, J. M., Young, L., Farrell, K. & Steller, H. Genetic control of programmed cell death in *Drosophila*. *Science* 264, 677-683 (1994).
10. Du, C., Fang, M., Li, Y., Li, L. & Wang, X. Smac, a mitochondrial protein that promotes cytochrome c-dependent caspase activation by eliminating IAP proteins. *Cell* 102, 33-42 (2000).

11. Verhagen, A. et al. Identification of DIABLO, a mammalian protein that promotes apoptosis by binding to and antagonizing IAP proteins. *Cell* 102, 43-54 (2000).
12. Hegde, R. et al. Identification of Omi/HtrA2 as a mitochondrial apoptotic serine protease that disrupts IAP-caspase interaction. *J. Biol. Chem.* 277, 432-438 (2002).
13. Martins, L. M. et al. The serine protease Omi/HtrA2 regulates apoptosis by binding XIAP through a Reaper-like motif *J. Biol. Chem.* 277, 439-444 (2002).
14. Suzuki, Y. et al. A serine protease, HtrA2, is released from the mitochondria and interacts with XIAP, inducing cell death *Mol. Cell* 8, 613-621 (2001).
15. Verhagen, A. et al. HtrA2 promotes cell death through its serine protease activity and its ability to antagonise inhibitor of apoptosis proteins. *J. Biol. Chem.* 277, 445-454 (2001).
16. Joazeiro, C. A. & Weissman, A. M. RING finger proteins: mediators of ubiquitin ligase activity. *Cell* 102, 549-552 (2000).
17. Huang, H. K. et al. The inhibitor of apoptosis, cIAP2, functions as a ubiquitin protein ligase and promotes in vitro monoubiquitination of caspase 3 and 7. *J. Biol. Chem.* 275, 26661-26664 (2000).
18. Suzuki, Y., Nakabayashi, Y. & Takahashi, R. Ubiquitin-protein ligase activity of X-linked inhibitor of apoptosis protein promotes proteasomal degradation of caspase-3 and enhances its anti-apoptotic effect in Fas-induced cell death. *Proc. Natl. Acad. Sci. USA* 98, 8662-8667 (2001).
19. Yang, Y., Fang, S., Jensen, J. P., Weissman, A. M. & Ashwell, J. D. Ubiquitin protein ligase activity of IAPs and their degradation in proteasomes in response to apoptotic stimuli. *Science* 288, 874-877 (2000).
20. Blair, S. S. Mechnisms of compartment formation: evidence that non-proliferating cells do not play a critical role in defining the D/V lineage restriction in the developing wing of *Drosophila*. *Development* 119, 339-351 (1993).
21. Clem, R. J., Fechneimer, M. & Miller, L. K. Prevention of apoptosis by a baculovirus gene during infection of insect cells. *Science* 254, 1388-1390 (1991).
22. Brand, A. H. & Perrimon, N. Targeted gene expression as a means of modulateing cell fates and generating dominant phenotypes. *Development* 118, 401-415 (1993).
23. Baker, N. E. & Yu, S. Y. The EGF receptor defines domains of cell cycle progression and survival to regulate cell number in the developing *Drosophila* eye. *Cell* 104, 699-708 (2000).
24. Srinivasan, A. et al. In situ immunodetection of activated caspase-3 in apoptotic neurons in the developing nervous system. *Cell Death Differ.* 5, 1004-1016 (1998).
25. Bergmann, A., Agapite, J., McCall, K. & Steller, H. The *Drosophila* gene hid is a direct molecular target of Ras-dependent survival signaling. *Cell* 95, 331-341 (1998).
26. Kurada, P. & White, K. Ras promotes cell survival in *Drosophila* by downregulating hid expression. *Cell* 95, 319-329 (1998).
27. Wilson, P. et al. The RING finger of DIAP1 is essential for regulating apoptosis submitted to *Nat. Cell Biol.*
28. Saville, K. J. & Belote, J. M. Identification of an essential gene, l(3) 73Ai, with a dominant temperature-sensitive lethal allele, encoding a *Drosophila* proteasome subunit *Proc. Natl. Acad. Sci. USA* 90, 8842-8846 (1993).
29. Fischer-Vize, J. A., Rubin, G. M. & Lehmann, R. The fat facets gene is required for *Drosophila* eye and embryo development. *Development* 116, 985-1000 (1992).
30. Treier, M., Seufert, W. & Jentsch, S. *Drosophila* UbcD1 encodes a highly conserved ubiquitin conjugating enzyme involved in selective protein degradation *EMBO J.* 11, 367-372 (1992).
31. Cenci, G. et al. ubcD1, a *Drosophila* ubiquitin-conjugating enzyme required for proper telomere behavior *Genes Dev.* 11, 863-875 (1997).
32. Neufeld, T. P., Tang, A. H. & Rubin G. M. A genetic screen to identify components of the sina signaling pathway in *Drosophila* eye development *Genetics* 148, 277-286 (1998).
33. Matuschewski, K., Hauser, H. P., Treier, M. & Jentsch, S. Identification of a novel family of ubiquitin-conjugating enzymes with distinct amino-terminal extensions. *J. Biol Chem.* 271, 2789-2794 (1996).
34. Meier, P., Silke, J., Leevers, S. J. & Evan, G. I. The *Drosophila* caspase DRONC is regulated by DIAP1. *EMBO J.* 19, 598-611(2000).
35. Quinn, L. M. et al. An essential role for the caspase dronc in developmentally programmed cell death in *Drosophila*. *J. Biol. Chem.* 275, 40416-40424 (2000).
36. Xu, T. & Rubin, G. M. Analysis of genetic mosaics in developing and adult *Drosophila* tissues. *Development* 117, 1223-1237 (1993).
37. Kanuka, H. et al. Control of the cell death pathway by Dapaf-1, a *Drosophila* Apaf-1/CED-4-related caspase activator. *Mol. Cell* 4, 757-769 (1999).
38. Rodriguez, A. et al. Dark is a *Drosophila* homologue of Apaf-1/CED-4 and functions in an evolutionarily conserved death pathway. *Nat. Cell Biol.* 1, 272-279 (1999).
39. Gaumer, S., Guenal, I., Brun, S., Theodore, L. & Mignotte, B. bcl-2 and bax mammalian regulators of apoptosis are functional in *Drosophila*. *Cell Death Differ.* 7, 804-814 (2000).
40. Baehrecke, E. H. Steroid regulation of programmed cell death during *Drosophila* development *Cell Death Differ.* 7, 1057-1062 (2000).
41. Lee, C. Y. et al. E93 directs steroid-triggered programmed cell death in *Drosophila*. *Mol Cell* 6, 433-443 (2000).
42. Jiang C., Lamblin, A. F., Steller H. & Thummel C. S. A steroid-triggered transcriptional hierarchy controls salivary gland cell death during *Drosophila* metamorphosis. *Mol. Cell* 5, 445-455.
43. Christich, A. et al. The damage-responsive *Drosophila* gene sickle encodes a novel IAP binding protein similar to but distinct from reaper. *Curr. Biol.* 12, 137-140 (2002).
44. Srinivasula, S. et al. sickle, a novel *Drosophila* death gene in the reaper/hid/grim region, encodes an IAP-inhibitory protein *Curr. Biol.* 12, 125-130 (2002).
45. Wing, J. P., Zhou, L., Schwartz, L. M. & Nambu, J. R. Distinct cell killing properties of the *Drosophila* reaper, head involution defective, and grim genes. *Cell Death Differ.* 5, 930-939 (1998).
46. White, K., Tahaoglu, E. & Steller, H. Cell killing by the *Drosophila* gene reaper. *Science* 271, 805-807 (1996).
47. Grether, M. E., Abrams, J. M., Agapite, J., White, K. & Steller, H. The head involution defective gene of *Drosophila melanogaster* functions in programmed cell death. *Genes Dev.* 9, 1694-1708 (1995).
48. Zhou, L. et al. Cooperative functions of the reaper and head involution defective genes in programmed cell death of *Drosophila* CNS midline cells. *Proc. Natl. Acad. Sci. USA* 94, 5131-5136.
49. Spradling, A. C. et al. The Berkeley *Drosophila* Genome Project gene disruption project: Single P-element insertions mutating 25% of vital *Drosophila* genes. *Genetics* 153, 135-177 (1999).
50. Calleja, M. & Morata, G. Visualization of gene expression in living adult *Drosophila*. *Science* 274, 252-255 (1996).
51. Cohen, B., Simcox, A. A. & Cohen, S. M. Allocation of the thoracic imaginal primordia in the *Drosophila* embryo. *Development* 117, 597-608 (1993).

What is claimed is:

1. An isolated peptide, said peptide comprising the amino acid sequence of SEQ ID NO: 38, 39, 40, 42, 44, 45, 46, 47, or 61.

2. The isolated peptide of claim 1, wherein said peptide comprises the amino acid sequence of SEQ ID No: 61.

3. The isolated peptide of claim 1, wherein said peptide comprises the amino acid sequence of SEQ ID No: 38.

4. The isolated peptide of claim 1, wherein said peptide is encoded by the nucleotide sequence of SEQ ID No: 51.

5. A composition comprising the isolated peptide of claim 1.

* * * * *